US007081350B2

(12) United States Patent
O'Connor et al.

(10) Patent No.: US 7,081,350 B2
(45) Date of Patent: Jul. 25, 2006

(54) METHODS FOR IDENTIFYING ECDYSTEROID SYNTHESIS INHIBITORS USING THE DROSOPHILA P450 ENZYME SHADE

(75) Inventors: Michael O'Connor, Roseville, MN (US); Lawrence I. Gilbert, Chapel Hill, NC (US); James T. Warren, Durham, NC (US)

(73) Assignees: Regents of the University of Minnesota, Minneapolis, MN (US); University of North Carolina, Chapel Hill, NC (US)

( * ) Notice: Subject to any disclaimer, the term of this patent is extended or adjusted under 35 U.S.C. 154(b) by 134 days.

(21) Appl. No.: 10/236,433

(22) Filed: Sep. 6, 2002

(65) Prior Publication Data

US 2003/0100025 A1 May 29, 2003

Related U.S. Application Data

(60) Provisional application No. 60/318,006, filed on Sep. 7, 2001, provisional application No. 60/317,890, filed on Sep. 7, 2001.

(51) Int. Cl.
  *G01N 33/53* (2006.01)
  *C12N 9/02* (2006.01)
(52) U.S. Cl. .................. 435/7.2; 435/189; 435/7.71; 435/252.3; 435/320.1; 435/6; 530/350
(58) Field of Classification Search ............... 435/7.71, 435/189, 6, 252.3, 320.1, 7.2; 530/350
See application file for complete search history.

(56) References Cited

U.S. PATENT DOCUMENTS

| 5,459,130 | A | 10/1995 | Borovsky et al. |
| 5,501,976 | A | 3/1996 | Borovsky et al. |
| 5,753,249 | A | 5/1998 | Schwab |
| 6,123,756 | A | 9/2000 | Poppen et al. |

FOREIGN PATENT DOCUMENTS

| WO | WO 97/20469 | 6/1997 |
| WO | WO 97/45731 | 12/1997 |
| WO | WO 99/36520 | 7/1999 |
| WO | WO 00/15791 | 3/2000 |
| WO | WO 00/71678 | 11/2000 |
| WO | WO 01/02436 | 1/2001 |
| WO | WO 01/71042 | * 9/2001 |

OTHER PUBLICATIONS

Mitchell et al. Effects of the Neem Tree Compounds Azadirachtin, Salannin, Nimbin, and 6-Desacetylnimbin on Ecdysone 20-Monooxygenase Activity. Archives of Insect Biochemistry and Physiology (1997) 35:199-209.*

Petryk et al. Shade is the Drosophila P450 enzyme that mediates the hydroxylation of ecdysone to the steroid insect molyting hormone 20-hydroxyecdysone. PNAS (2003) 100(24): 13773-13778.*

Shirai et al. Monoclonal antibodies specific for ecdysone. Appl. Ent. Zool. (1991) 26(3); 335-341.*

Borrebaeck Antibodies in diagnostics—from immunoassays to protein chips. Immunology Today (2000) 21(8): 379-382.*

Warren et al. Molecular and biochemical characterization of two P450 enzymes in the ecdysteroidogenic pathway of Drosophila melanogaster. PNAS (2002 99(17): 11043-11048.*

Addison, "Safety Testing of Tebufenozide, a New Molt-Inducing Insecticide, for Effects Nontarget Forest Soil Invertebrates," *Ecotoxicol. Environ. Saf.*, 1996, 33:55-61.

Apoptosis—"Fruit Fly Experiments Show Hormones Triggering Cell Death," *Genomics & Genetics Weekly*, Apr. 7, 2000, pp. 4-5, NewsRx.com.

Aribi et al., "2-Deoxyecdysone is a circulating ecdysteroid in the beetle *Zophobas atratus,*" *Biochim. Biophys. Acta*, 1997, 1335:246-252.

Ashok and Dutta-Gupta, "In Vitro Effect of Nonsteroidal Ecdysone Agonist RH 5849 on Fat Body Acid Phosphatase Activity in Rice Moth, *Corcyra cephalonica* (Insecta),". *Biochem. Int.*, 1991, 24:69-75.

Bender et al., "Drosophila Ecdysone Receptor Mutations Reveal Functional Differences among Receptor Isoforms," *Cell*, 1997, 91:777-788.

Berndt and Kremer, "Insektenhormone zur Bekämpfung von Gesundheitsschädlingen," *Z. Gesamte Hyg.*, 1977, 23(8):521-528, Non-English.

Bowers, "Insect Hormones and Their Derivatives as Insecticides," *Bull. World Health Org.*, 1971, 44:381-389.

Buszczak et al., "Ecdysone response genes govern egg chamber development during mid-oogenesis in *Drosophila,*" *Development*, 1999, 126:4581-4589.

Carney and Bender, "The Drosophila *ecdysone receptor* (*EcR*) Gene Is Required Maternally for Normal Oogenesis," *Genetics*, 2000, 154:1203-1211.

Chávez et al., "The *Drosophila disembodied* gene controls late embryonic morphogenesis and codes for a cytochrome P450 enzyme that regulates embryonic ecdysone levels," *Development*, 2000, 127:4115-4126.

(Continued)

*Primary Examiner*—Chih-Min Kam
(74) *Attorney, Agent, or Firm*—Fish & Richardson P.C.

(57) ABSTRACT

The invention relates to methods and materials useful for identifying inhibitors of ecdysteroid biosynthetic enzymes, specifically the *Drosophila* P450 enzyme, shade. These methods and materials can be used, for example, to identify molecules having insecticidal properties.

4 Claims, 3 Drawing Sheets

OTHER PUBLICATIONS

Chen et al., "Baculovirus Expression and Purification of Human and Rat Cytochrome P450 2E1," *Arch. Biochem. Biophys.*, 1996, 335:123-130.

Farkaš Sláma, "Effect of bisacylhydrazine ecdysteroid mimics (RH-5849 and RH-5992) on chromosomal puffing, imaginal disc proliferation and pupariation in larvae of *Drosphila melanogaster*," *Insect Biochem. Mol Biol.*, 1999,, 29:1015-1027.

Gates and Thummel, "An Enhancer Trap Screen for Ecdysone-Inducible Genes Required for Drosophila Adult Leg Morphogenesis," *Genetics*, 2000, 156:1765-1776.

Ghoneim et al., "Effectiveness of the Non-Steroidal Ecdysone Mimic, RH-5849 for the Control of *Musca Domestica Vicina*," *J. Egyptian Parasitology*, 1991, 21(3):723-733.

Gilbert et al., "Control and Biochemical Nature of the Ecdysteroidogenic Pathway," *Annu. Rev. Entomol.*, 2002, 47:883-916.

Grieneisen et al., "Early Steps in Ecdysteroid Biosynthesis: Evidence for the Involvement of Cytochrome P-450 Enzymes," *Insect. Biochem. Molec. Biol.*, 1993, 23:13-23.

Grieneisen, "Recent Advances in our Knowledge of Ecdysteroid Biosynthesis in Insects and Crustaceans," *Insect Biochem. Molec. Biol.*, 1994, 24(2):115-132.

Henrich et al., "Peptide Hormones, Steroid Hormones, and Puffs: Mechanisms and Models in Insect Development," *Vitamins and Hormones*, vol. 55, Litwack (ed.), 1999, Academic Press, San Diego, pp. 73-125.

Keogh and Smith, "Regulation of Cytochrome P-450 Dependent Steroid Hydroxylase Activity in *Manduca Sexta*: Effects of the Ecdysone Agonist RH 5849 on Ecdysone 20-Monooxygenase Activity," *Biochem. Biophys. Res. Comm.*, 1991, 176:522-527.

Kostyukovsky et al., "Biological activity of two juvenoids and two ecdysteroids against three stored product insects," *Insect Biochem. Mol. Biol.*, 2000, 30:891-897.

Koul and Kapil, "RH-5849, a nonsteroidal ecdysone agonist, does not mimic makisterone-A in *Dysdercus koenigii*," *Experientia*, 1994, 50(5):461-464.

Kreutzweiser et al., "Toxicity of a New Molt-Inducing Insecticide (RH-5992) to Aquatic Macroinvertebrates," *Ecotoxicol. Environ. Saf.*, 1994, 28:14-24.

Nelson, "Cytochrome P450 Nomenclature," *Methods in Molecular Biology*, vol. 107, Cytochrome P450 Protocols, Phillips and Shephard (eds.), 1998, Humana Press, Totowa, New Jersey, pp. 15-24.

Pascual et al., "Quantification of Ecdysteroids by Immunoassay: Comparison of Enzyme Immunoassay and Radioimmunoassay," *J. Biosciences*, 1995, 50(11/12):862-867.

Peterson et al., "Methoprene and 20-OH-Ecdysone Affect Male Production in *Daphnia pulex*," *Environ. Toxicol. Chem.*, 2001, 20(3):582-588.

Porcheron et al., "Development of an Enzyme Immunoassay for Ecdysteroids Using Acetylcholinesterase as Label," *Insect Biochem.*, 1989, 19(2):117-122.

Riddiford, "Hormones and *Drosophila* Development," *The Development of Drosophila melanogaster*, vol. II, Bate and Arias (eds.), 1993, Cold Spring Harbor Laboratory Press, pp. 899-939.

Saez et al., "Identification of ligands and coligands for the ecdysone-regulated gene switch," *Proc. Natl. Acad. Sci. USA*, 2000, 97(26):14512-14517.

Šorm, "Insect Hormones and Their Bioanalogues as Potential Insecticides," *FEBS Letters*, 1974, 40(Suppl.):S128-S132.

Spiegelman et al., "The Expression of Insecticide Resistance-Related Cytochrome P450 Forms Is Regulated by Molting Hormone in *Drosophila melanogaster*," *Biochem. Biophys. Res. Comm.*, 1997, 232:304-307.

Sundaram et al., "BAsis for selective action of a synthetic molting hormone agonist, RH-5992 on lepidopteran insects," *Insect Biochem. Mol. Biol.*, 1998, 28:693-704.

Warbrick et al., "The effect of invertebrate hormones and potential hormone inhibitors on the third larval moult of the filarial nematode, *Dirofilaria immitis, in vitro*," *Parasitology*, 1993, 107:459-463.

Warren et al., "Differential Incorporation of Cholesterol and Cholesterol Derivatives Into Ecdysteroids by the Larval Ring Glands and Adult Ovaries of *Drosophila melanogaster*: a Putative Explanation for the 1(3)$ecd^1$ Mutation," *Insect. Biochem. Molec. Biol.*, 1996, 26(8-9):931-943.

Warren et al., "Molecular and biochemical characterization of two P450 enzymes in the ecdysteroidogenic pathway of *Drosophila melanogaster*," *Proc. Natl. Acad. Sci. USA*, 2002, 99(17):11043-11048.

Wing, "RH 5849, a Nonsteroidal Ecdysone Agonist: Effects on a *Drosophila* Cell Line," *Science*, 1988, 241:467-469.

* cited by examiner

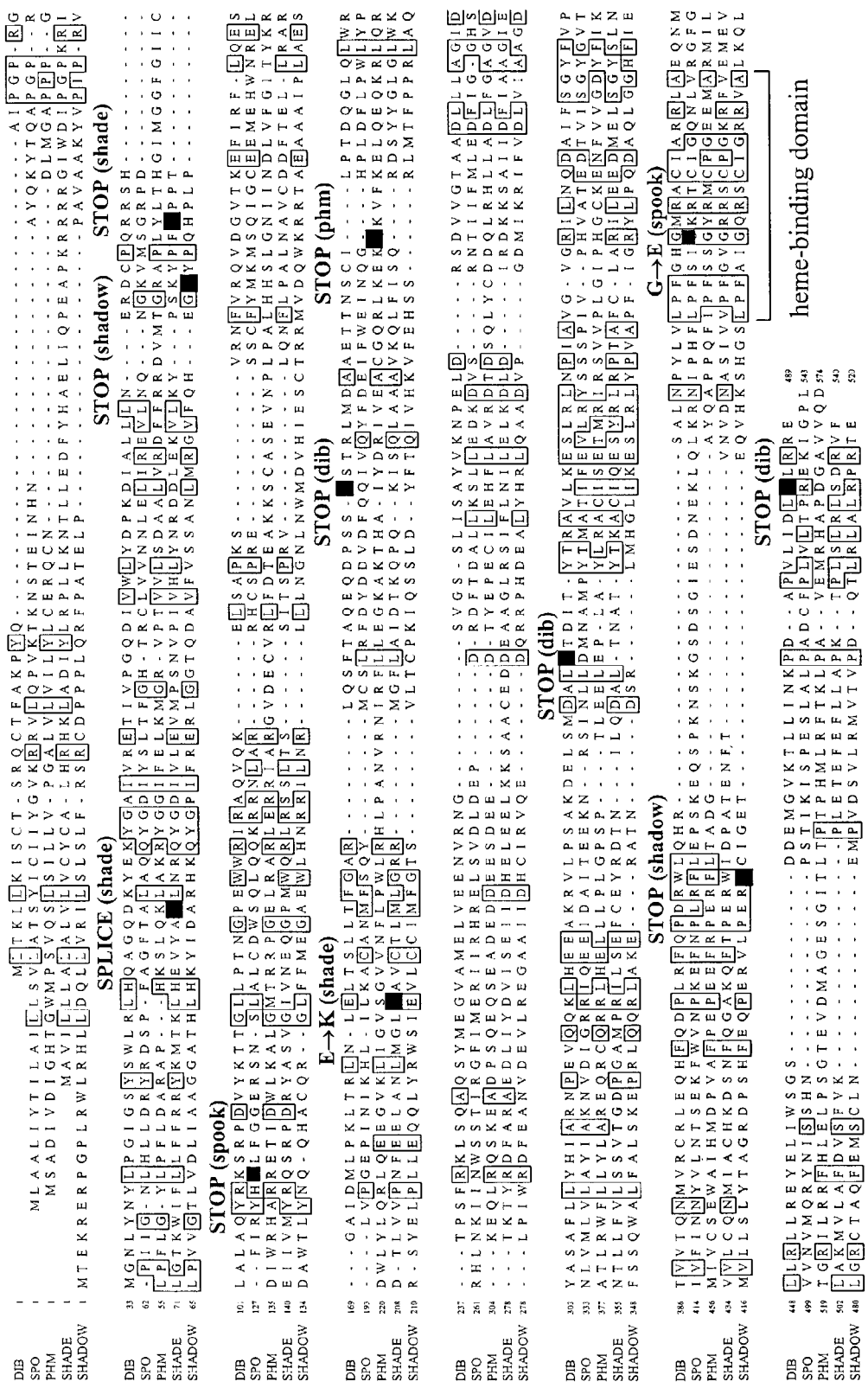
Figure 1: Alignment of Novel P450 Enzymes & Mutants

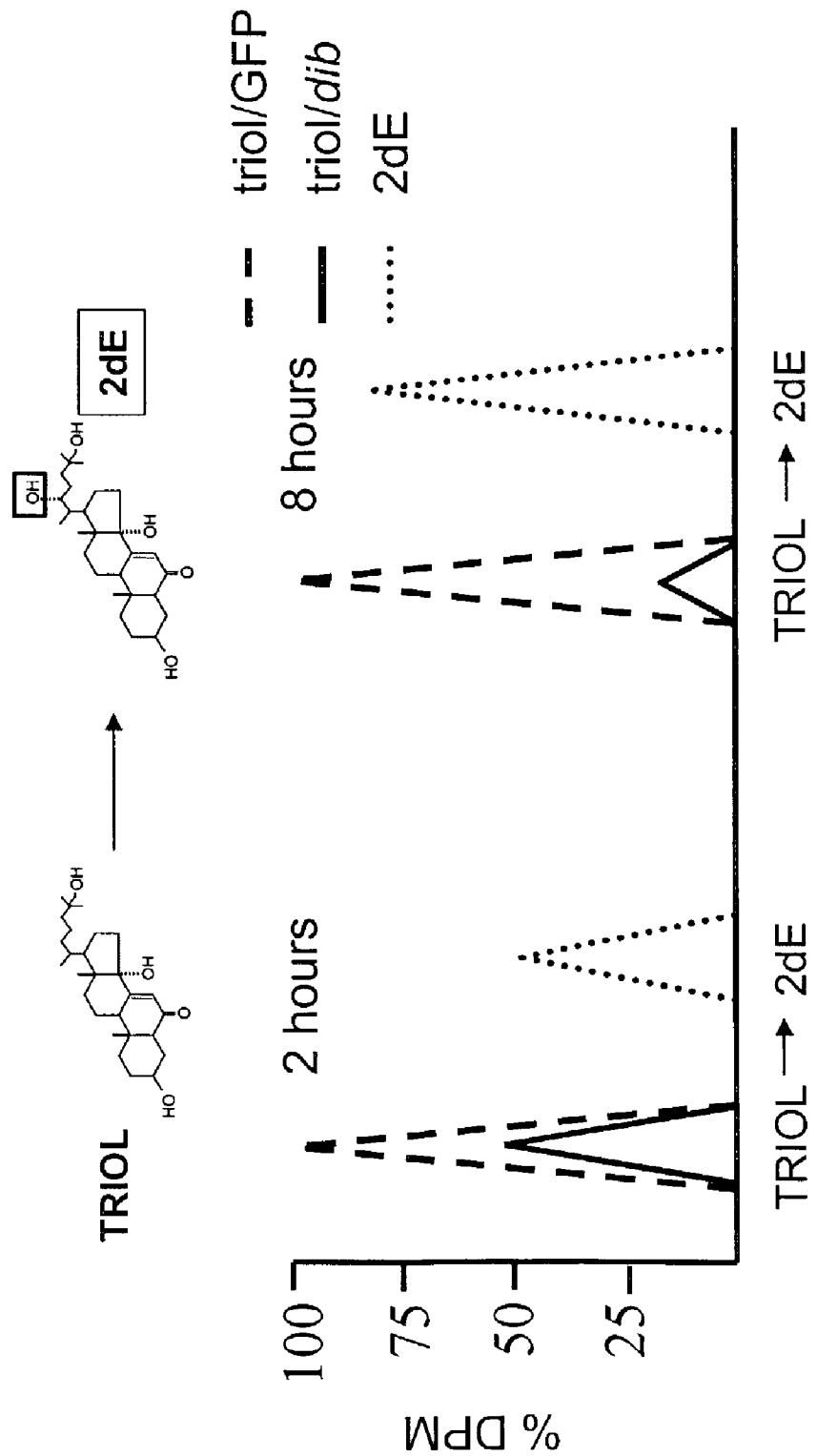
Figure 2: HPLC Analysis of CYP302a1 Catalytic Activity

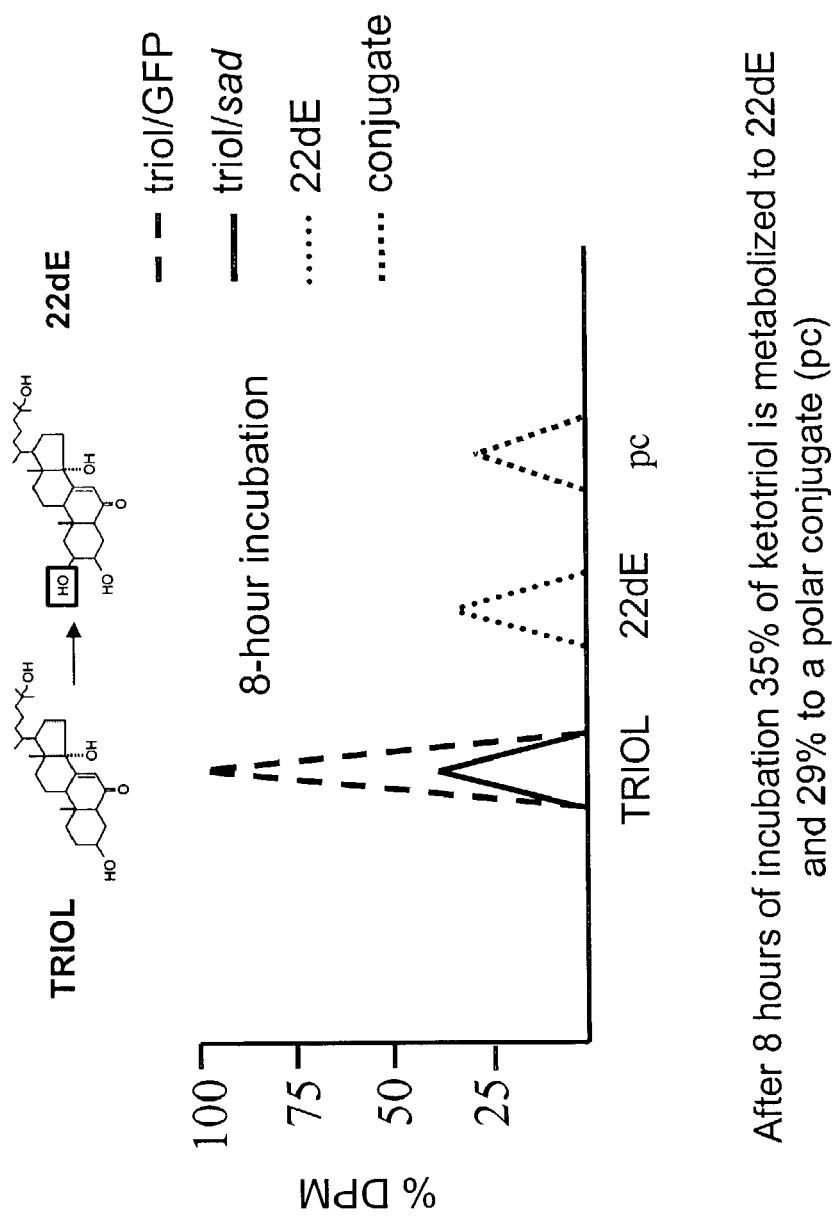
Figure 3: HPLC Analysis of CYP315a1 Catalytic Activity
After 8 hours of incubation 35% of ketotriol is metabolized to 22dE and 29% to a polar conjugate (pc)

SEQUENCE LISTING

<160> NUMBER OF SEQ ID NOS: 18

<210> SEQ ID NO 1
<211> LENGTH: 489
<212> TYPE: PRT
<213> ORGANISM: Drosophila

<400> SEQUENCE: 1

```
Met Leu Thr Lys Leu Leu Lys Ile Ser Cys Thr Ser Arg Gln Cys Thr
  1               5                  10                  15

Phe Ala Lys Pro Tyr Gln Ala Ile Pro Gly Pro Arg Gly Pro Phe Gly
                 20                  25                  30

Met Gly Asn Leu Tyr Asn Tyr Leu Pro Gly Ile Gly Ser Tyr Ser Trp
             35                  40                  45

Leu Arg Leu His Gln Ala Gly Gln Asp Lys Tyr Glu Lys Tyr Gly Ala
         50                  55                  60

Ile Val Arg Glu Thr Ile Val Pro Gly Gln Asp Ile Val Trp Leu Tyr
 65                  70                  75                  80

Asp Pro Lys Asp Ile Ala Leu Leu Asn Glu Arg Asp Cys Pro Gln
                 85                  90                  95

Arg Arg Ser His Leu Ala Leu Ala Gln Tyr Arg Lys Ser Arg Pro Asp
                100                 105                 110

Val Tyr Lys Thr Thr Gly Leu Leu Pro Thr Asn Gly Pro Glu Trp Trp
            115                 120                 125

Arg Ile Arg Ala Gln Val Gln Lys Glu Leu Ser Ala Pro Lys Ser Val
        130                 135                 140

Arg Asn Phe Val Arg Gln Val Asp Gly Val Thr Lys Glu Phe Ile Arg
145                 150                 155                 160

Phe Leu Gln Glu Ser Arg Asn Gly Gly Ala Ile Asp Met Leu Pro Lys
                165                 170                 175

Leu Thr Arg Leu Asn Leu Glu Leu Thr Ser Leu Thr Phe Gly Ala
            180                 185                 190

Arg Leu Gln Ser Phe Thr Ala Gln Glu Gln Asp Pro Ser Ser Arg Ser
        195                 200                 205

Thr Arg Leu Met Asp Ala Ala Glu Thr Thr Asn Ser Cys Ile Leu Pro
210                 215                 220

Thr Asp Gln Gly Leu Gln Leu Trp Arg Phe Leu Glu Thr Pro Ser Phe
225                 230                 235                 240

Arg Lys Leu Ser Gln Ala Gln Ser Tyr Met Glu Gly Val Ala Met Glu
                245                 250                 255

Leu Val Glu Glu Asn Val Arg Asn Gly Ser Val Gly Ser Ser Leu Ile
            260                 265                 270

Ser Ala Tyr Val Lys Asn Pro Glu Leu Asp Arg Ser Asp Val Val Gly
        275                 280                 285

Thr Ala Ala Asp Leu Leu Leu Ala Gly Ile Asp Thr Thr Ser Tyr Ala
    290                 295                 300

Ser Ala Phe Leu Leu Tyr His Ile Ala Arg Asn Pro Glu Val Gln Gln
```

```
                305                 310                 315                 320
Lys Leu His Glu Glu Ala Lys Arg Val Leu Pro Ser Ala Lys Asp Glu
                    325                 330                 335

Leu Ser Met Asp Ala Leu Arg Thr Asp Ile Thr Tyr Thr Arg Ala Val
                340                 345                 350

Leu Lys Glu Ser Leu Arg Leu Asn Pro Ile Ala Val Gly Val Gly Arg
                355                 360                 365

Ile Leu Asn Gln Asp Ala Ile Phe Ser Gly Tyr Phe Val Pro Lys Gly
            370                 375                 380

Thr Thr Val Val Thr Gln Asn Met Val Arg Cys Arg Leu Glu Gln His
385                 390                 395                 400

Phe Gln Asp Pro Leu Arg Phe Gln Pro Asp Arg Trp Leu Gln His Arg
                405                 410                 415

Ser Ala Leu Asn Pro Tyr Leu Val Leu Pro Phe Gly His Gly Met Arg
                420                 425                 430

Ala Cys Ile Ala Arg Arg Leu Ala Glu Gln Asn Met His Ile Leu Leu
                435                 440                 445

Leu Arg Leu Leu Arg Glu Tyr Glu Leu Ile Trp Ser Gly Ser Asp Asp
450                 455                 460

Glu Met Gly Val Lys Thr Leu Leu Ile Asn Lys Pro Asp Ala Pro Val
465                 470                 475                 480

Leu Ile Asp Leu Arg Leu Arg Arg Glu
                485

<210> SEQ ID NO 2
<211> LENGTH: 574
<212> TYPE: PRT
<213> ORGANISM: Drosophila

<400> SEQUENCE: 2

Met Ser Ala Asp Ile Val Asp Ile Gly His Thr Gly Trp Met Pro Ser
1               5                   10                  15

Val Gln Ser Leu Ser Ile Leu Val Pro Gly Ala Leu Val Leu Val
                20                  25                  30

Ile Leu Tyr Leu Cys Glu Arg Gln Cys Asn Asp Leu Met Gly Ala Pro
                35                  40                  45

Pro Pro Gly Pro Trp Gly Leu Pro Phe Leu Gly Tyr Leu Pro Phe Leu
                50                  55                  60

Asp Ala Arg Ala Pro His Lys Ser Leu Gln Lys Leu Ala Lys Arg Tyr
65              70                  75                  80

Gly Gly Ile Phe Glu Leu Lys Met Gly Arg Val Pro Thr Val Val Leu
                85                  90                  95

Ser Asp Ala Ala Leu Val Arg Asp Phe Phe Arg Arg Asp Val Met Thr
                100                 105                 110

Gly Arg Ala Pro Leu Tyr Leu Thr His Gly Ile Met Gly Gly Phe Gly
                115                 120                 125

Ile Ile Cys Ala Gln Glu Asp Ile Trp Arg His Ala Arg Arg Glu Thr
            130                 135                 140

Ile Asp Trp Leu Lys Ala Leu Gly Met Thr Arg Arg Pro Gly Glu Leu
145                 150                 155                 160

Arg Ala Arg Leu Glu Arg Ile Ala Arg Gly Val Asp Glu Cys Val
                    165                 170                 175

Arg Leu Phe Asp Thr Glu Ala Lys Lys Ser Cys Ala Ser Glu Val Asn
                180                 185                 190
```

-continued

Pro Leu Pro Ala Leu His His Ser Leu Gly Asn Ile Ile Asn Asp Leu
        195                 200                 205

Val Phe Gly Ile Thr Tyr Lys Arg Asp Asp Pro Asp Trp Leu Tyr Leu
        210                 215                 220

Gln Arg Leu Gln Glu Glu Gly Val Lys Leu Ile Gly Val Ser Gly Val
225                 230                 235                 240

Val Asn Phe Leu Pro Trp Leu Arg His Leu Pro Ala Asn Val Arg Asn
                245                 250                 255

Ile Arg Phe Leu Leu Glu Gly Lys Ala Lys Thr His Ala Ile Tyr Asp
                260                 265                 270

Arg Ile Val Glu Ala Cys Gly Gln Arg Leu Lys Glu Lys Gln Lys Val
            275                 280                 285

Phe Lys Glu Leu Gln Glu Gln Lys Arg Leu Gln Arg Gln Leu Glu Lys
        290                 295                 300

Glu Gln Leu Arg Gln Ser Lys Glu Ala Asp Pro Ser Gln Glu Gln Ser
305                 310                 315                 320

Glu Ala Asp Glu Asp Asp Glu Glu Ser Asp Glu Asp Thr Tyr Glu
                325                 330                 335

Pro Glu Cys Ile Leu Glu His Phe Leu Ala Val Arg Asp Thr Asp Ser
                340                 345                 350

Gln Leu Tyr Cys Asp Asp Gln Leu Arg His Leu Leu Ala Asp Leu Phe
            355                 360                 365

Gly Ala Gly Val Asp Thr Ser Leu Ala Thr Leu Arg Trp Phe Leu Leu
        370                 375                 380

Tyr Leu Ala Arg Glu Gln Arg Cys Gln Arg Arg Leu His Glu Leu Leu
385                 390                 395                 400

Leu Pro Leu Gly Pro Ser Pro Thr Leu Glu Glu Leu Glu Pro Leu Ala
                405                 410                 415

Tyr Leu Arg Ala Cys Ile Ser Glu Thr Met Arg Ile Arg Ser Val Val
                420                 425                 430

Pro Leu Gly Ile Pro His Gly Cys Lys Glu Asn Phe Val Val Gly Asp
            435                 440                 445

Tyr Phe Ile Lys Gly Gly Ser Met Ile Val Cys Ser Glu Trp Ala Ile
        450                 455                 460

His Met Asp Pro Val Ala Phe Pro Glu Pro Glu Glu Phe Arg Pro Glu
465                 470                 475                 480

Arg Phe Leu Thr Ala Asp Gly Ala Tyr Gln Ala Pro Pro Gln Phe Ile
                485                 490                 495

Pro Phe Ser Ser Gly Tyr Arg Met Cys Pro Gly Glu Glu Met Ala Arg
                500                 505                 510

Met Ile Leu Thr Leu Phe Thr Gly Arg Ile Leu Arg Arg Phe His Leu
        515                 520                 525

Glu Leu Pro Ser Gly Thr Glu Val Asp Met Ala Gly Glu Ser Gly Ile
530                 535                 540

Thr Leu Thr Pro Thr Pro His Met Leu Arg Phe Thr Lys Leu Pro Ala
545                 550                 555                 560

Val Glu Met Arg His Ala Pro Asp Gly Ala Val Val Gln Asp
                565                 570

<210> SEQ ID NO 3
<211> LENGTH: 543
<212> TYPE: PRT
<213> ORGANISM: Drosophila

<400> SEQUENCE: 3

-continued

```
Met Leu Ala Ala Leu Ile Tyr Thr Ile Leu Ala Ile Leu Leu Ser Val
 1               5                   10                  15

Leu Ala Thr Ser Tyr Ile Cys Ile Ile Tyr Gly Val Lys Arg Arg Val
             20                  25                  30

Leu Gln Pro Val Lys Thr Lys Asn Ser Thr Glu Ile Asn His Asn Ala
         35                  40                  45

Tyr Gln Lys Tyr Thr Gln Ala Pro Gly Pro Arg Pro Trp Pro Ile Ile
 50                  55                  60

Gly Asn Leu His Leu Leu Asp Arg Tyr Arg Asp Ser Pro Phe Ala Gly
 65              70                  75                  80

Phe Thr Ala Leu Ala Gln Gln Tyr Gly Asp Ile Tyr Ser Leu Thr Phe
             85                  90                  95

Gly His Thr Arg Cys Leu Val Val Asn Leu Glu Leu Ile Arg Glu
                100                 105                 110

Val Leu Asn Gln Asn Gly Lys Val Met Ser Gly Arg Pro Asp Phe Ile
         115                 120                 125

Arg Tyr His Lys Leu Phe Gly Gly Glu Arg Ser Asn Ser Leu Ala Leu
 130                 135                 140

Cys Asp Trp Ser Gln Leu Gln Gln Lys Arg Arg Asn Leu Ala Arg Arg
145                 150                 155                 160

His Cys Ser Pro Arg Glu Ser Ser Cys Phe Tyr Met Lys Met Ser Gln
                165                 170                 175

Ile Gly Cys Glu Glu Met Glu His Trp Asn Arg Glu Leu Gly Asn Gln
                180                 185                 190

Leu Val Pro Gly Glu Pro Ile Asn Ile Lys His Leu Ile Leu Lys Ala
         195                 200                 205

Cys Ala Asn Met Phe Ser Gln Tyr Met Cys Ser Leu Arg Phe Asp Tyr
210                 215                 220

Asp Asp Val Asp Phe Gln Gln Ile Val Gln Tyr Phe Asp Glu Ile Phe
225                 230                 235                 240

Trp Glu Ile Asn Gln Gly His Pro Leu Asp Phe Leu Pro Trp Leu Tyr
                245                 250                 255

Pro Phe Tyr Gln Arg His Leu Asn Lys Ile Ile Asn Trp Ser Ser Thr
            260                 265                 270

Ile Arg Gly Phe Ile Met Glu Arg Ile Arg His Arg Glu Leu Ser
            275                 280                 285

Val Asp Leu Asp Glu Pro Asp Arg Asp Phe Thr Asp Ala Leu Leu Lys
        290                 295                 300

Ser Leu Leu Glu Asp Lys Asp Val Ser Arg Asn Thr Ile Ile Phe Met
305                 310                 315                 320

Leu Glu Asp Phe Ile Gly Gly His Ser Ala Val Gly Asn Leu Val Met
                325                 330                 335

Leu Val Leu Ala Tyr Ile Ala Lys Asn Val Asp Ile Gly Arg Arg Ile
            340                 345                 350

Gln Glu Glu Ile Asp Ala Ile Thr Glu Glu Lys Asn Arg Ser Ile Asn
        355                 360                 365

Leu Leu Asp Met Asn Ala Met Pro Tyr Thr Met Ala Thr Ile Phe Glu
370                 375                 380

Val Leu Arg Tyr Ser Ser Ser Pro Ile Val Pro His Val Ala Thr Glu
385                 390                 395                 400

Asp Thr Val Ile Ser Gly Tyr Gly Val Thr Lys Gly Thr Ile Val Phe
                405                 410                 415
```

-continued

```
Ile Asn Asn Tyr Val Leu Asn Thr Ser Glu Lys Phe Trp Val Asn Pro
            420                 425                 430

Lys Glu Phe Asn Pro Leu Arg Phe Leu Glu Pro Ser Lys Glu Gln Ser
        435                 440                 445

Pro Lys Asn Ser Lys Gly Ser Asp Ser Gly Ile Glu Ser Asp Asn Glu
    450                 455                 460

Lys Leu Gln Leu Lys Arg Asn Ile Pro His Phe Leu Pro Phe Ser Ile
465                 470                 475                 480

Gly Lys Arg Thr Cys Ile Gly Gln Asn Leu Val Arg Gly Phe Gly Phe
                485                 490                 495

Leu Val Val Asn Val Met Gln Arg Tyr Asn Ile Ser Ser His Asn
            500                 505                 510

Pro Ser Thr Ile Lys Ile Ser Pro Glu Ser Leu Ala Leu Pro Ala Asp
        515                 520                 525

Cys Phe Pro Leu Val Leu Thr Pro Arg Glu Lys Ile Gly Pro Leu
    530                 535                 540
```

<210> SEQ ID NO 4
<211> LENGTH: 540
<212> TYPE: PRT
<213> ORGANISM: Drosophila

<400> SEQUENCE: 4

```
Met Ala Val Ile Leu Leu Ala Leu Ala Leu Val Leu Gly Cys Tyr
1               5                   10                  15

Cys Ala Leu His Arg His Lys Leu Ala Asp Ile Tyr Leu Arg Pro Leu
            20                  25                  30

Leu Lys Asn Thr Leu Leu Glu Asp Phe Tyr His Ala Glu Leu Ile Gln
        35                  40                  45

Pro Glu Ala Pro Lys Arg Arg Arg Gly Ile Trp Asp Ile Pro Gly
    50                  55                  60

Pro Lys Arg Ile Pro Phe Leu Gly Thr Lys Trp Ile Phe Leu Leu Phe
65                  70                  75                  80

Phe Arg Arg Tyr Lys Met Thr Lys Leu His Glu Val Tyr Ala Asp Leu
                85                  90                  95

Asn Arg Gln Tyr Gly Asp Ile Val Leu Glu Val Met Pro Ser Asn Val
            100                 105                 110

Pro Ile Val His Leu Tyr Asn Arg Asp Leu Glu Lys Val Leu Lys
        115                 120                 125

Tyr Pro Ser Lys Tyr Pro Phe Arg Pro Thr Glu Ile Ile Val Met
    130                 135                 140

Tyr Arg Gln Ser Arg Pro Asp Arg Tyr Ala Ser Val Gly Ile Val Asn
145                 150                 155                 160

Glu Gln Gly Pro Met Trp Gln Arg Leu Arg Ser Ser Leu Thr Ser Ser
                165                 170                 175

Ile Thr Ser Pro Arg Val Leu Gln Asn Phe Leu Pro Ala Leu Asn Ala
            180                 185                 190

Val Cys Asp Asp Phe Ile Glu Leu Leu Arg Ala Arg Arg Asp Pro Asp
        195                 200                 205

Thr Leu Val Val Pro Asn Phe Glu Glu Leu Ala Asn Leu Met Gly Leu
    210                 215                 220

Glu Ala Val Cys Thr Leu Met Leu Gly Arg Arg Met Gly Phe Leu Ala
225                 230                 235                 240

Ile Asp Thr Lys Gln Pro Gln Lys Ile Ser Gln Leu Ala Ala Ala Val
                245                 250                 255
```

-continued

Lys Gln Leu Phe Ile Ser Gln Arg Asp Ser Tyr Tyr Gly Leu Gly Leu
          260                 265                 270

Trp Lys Tyr Phe Pro Thr Lys Thr Tyr Arg Asp Phe Ala Arg Ala Glu
          275                 280                 285

Asp Leu Ile Tyr Asp Val Ile Ser Glu Ile Ile Asp His Glu Leu Glu
          290                 295                 300

Glu Leu Lys Lys Ser Ala Ala Cys Glu Asp Glu Ala Ala Gly Leu
305                 310                 315                 320

Arg Ser Ile Phe Leu Asn Ile Leu Glu Leu Lys Asp Leu Asp Ile Arg
                325                 330                 335

Asp Lys Lys Ser Ala Ile Ile Asp Phe Ile Ala Gly Ile Glu Thr
                340                 345                 350

Leu Ala Asn Thr Leu Leu Phe Val Leu Ser Ser Val Thr Gly Asp Pro
          355                 360                 365

Gly Ala Met Pro Arg Ile Leu Ser Glu Phe Cys Glu Tyr Arg Asp Thr
          370                 375                 380

Asn Ile Leu Gln Asp Ala Leu Thr Asn Ala Thr Tyr Thr Lys Ala Cys
385                 390                 395                 400

Ile Gln Glu Ser Tyr Arg Leu Arg Pro Thr Ala Phe Cys Leu Ala Arg
                405                 410                 415

Ile Leu Glu Glu Asp Met Glu Leu Ser Gly Tyr Ser Leu Asn Ala Gly
                420                 425                 430

Thr Val Val Leu Cys Gln Asn Met Ile Ala Cys His Lys Asp Ser Asn
                435                 440                 445

Phe Gln Gly Ala Lys Gln Phe Thr Pro Glu Arg Trp Ile Asp Pro Ala
          450                 455                 460

Thr Glu Asn Phe Thr Val Asn Val Asp Asn Ala Ser Ile Val Val Pro
465                 470                 475                 480

Phe Gly Val Gly Arg Arg Ser Cys Pro Gly Lys Arg Phe Val Glu Met
                485                 490                 495

Glu Val Val Leu Leu Leu Ala Lys Met Val Leu Ala Phe Asp Val Ser
          500                 505                 510

Phe Val Lys Pro Leu Glu Thr Glu Phe Glu Phe Leu Leu Ala Pro Lys
          515                 520                 525

Thr Pro Leu Ser Leu Arg Leu Ser Asp Arg Val Phe
          530                 535                 540

<210> SEQ ID NO 5
<211> LENGTH: 520
<212> TYPE: PRT
<213> ORGANISM: Drosophila

<400> SEQUENCE: 5

Met Thr Glu Lys Arg Glu Arg Pro Gly Pro Leu Arg Trp Leu Arg His
1               5                   10                  15

Leu Leu Asp Gln Leu Leu Val Arg Ile Leu Ser Leu Ser Leu Phe Arg
                20                  25                  30

Ser Arg Cys Asp Pro Pro Leu Gln Arg Phe Pro Ala Thr Glu Leu
            35                  40                  45

Pro Pro Ala Val Ala Ala Lys Tyr Val Pro Ile Pro Arg Val Lys Gly
          50                  55                  60

Leu Pro Val Val Gly Thr Leu Val Asp Leu Ile Ala Ala Gly Gly Ala
65                  70                  75                  80

Thr His Leu His Lys Tyr Ile Asp Ala Arg His Lys Gln Tyr Gly Pro

-continued

```
                85                  90                  95
Ile Phe Arg Glu Arg Leu Gly Gly Thr Gln Asp Ala Val Phe Val Ser
            100                 105                 110
Ser Ala Asn Leu Met Arg Gly Val Phe Gln His Glu Gly Gln Tyr Pro
            115                 120                 125
Gln His Pro Leu Pro Asp Ala Trp Thr Leu Tyr Asn Gln Gln His Ala
            130                 135                 140
Cys Gln Arg Gly Leu Phe Phe Met Glu Gly Ala Glu Trp Leu His Asn
145                 150                 155                 160
Arg Arg Ile Leu Asn Arg Leu Leu Asn Gly Asn Leu Asn Trp Met
                165                 170                 175
Asp Val His Ile Glu Ser Cys Thr Arg Arg Met Val Asp Gln Trp Lys
            180                 185                 190
Arg Arg Thr Ala Glu Ala Ala Ala Ile Pro Leu Ala Glu Ser Gly Glu
            195                 200                 205
Ile Arg Ser Tyr Glu Leu Pro Leu Leu Glu Gln Gln Leu Tyr Arg Trp
            210                 215                 220
Ser Ile Glu Val Leu Cys Cys Ile Met Phe Gly Thr Ser Val Leu Thr
225                 230                 235                 240
Cys Pro Lys Ile Gln Ser Ser Leu Asp Tyr Phe Thr Gln Ile Val His
            245                 250                 255
Lys Val Phe Glu His Ser Ser Arg Leu Met Thr Phe Pro Pro Arg Leu
            260                 265                 270
Ala Gln Ile Leu Arg Leu Pro Ile Trp Arg Asp Phe Glu Ala Asn Val
            275                 280                 285
Asp Glu Val Leu Arg Glu Gly Ala Ala Ile Ile Asp His Cys Ile Arg
            290                 295                 300
Val Gln Glu Asp Gln Arg Arg Pro His Asp Glu Ala Leu Tyr His Arg
305                 310                 315                 320
Leu Gln Ala Ala Asp Val Pro Gly Asp Met Ile Lys Arg Ile Phe Val
            325                 330                 335
Asp Leu Val Ile Ala Ala Gly Asp Thr Thr Ala Phe Ser Ser Gln Trp
            340                 345                 350
Ala Leu Phe Ala Leu Ser Lys Glu Pro Arg Leu Gln Gln Arg Leu Ala
            355                 360                 365
Lys Glu Arg Ala Thr Asn Asp Ser Arg Leu Met His Gly Leu Ile Lys
            370                 375                 380
Glu Ser Leu Arg Leu Tyr Pro Val Ala Pro Phe Ile Gly Arg Tyr Leu
385                 390                 395                 400
Pro Gln Asp Ala Gln Leu Gly Gly His Phe Ile Glu Lys Asp Thr Met
            405                 410                 415
Val Leu Leu Ser Leu Tyr Thr Ala Gly Arg Asp Pro Ser His Phe Glu
            420                 425                 430
Gln Pro Glu Arg Val Leu Pro Glu Arg Trp Cys Ile Gly Glu Thr Glu
            435                 440                 445
Gln Val His Lys Ser His Gly Ser Leu Pro Phe Ala Ile Gly Gln Arg
            450                 455                 460
Ser Cys Ile Gly Arg Arg Val Ala Leu Lys Gln Leu His Ser Leu Leu
465                 470                 475                 480
Gly Arg Cys Ala Ala Gln Phe Glu Met Ser Cys Leu Asn Glu Met Pro
            485                 490                 495
Val Asp Ser Val Leu Arg Met Val Thr Val Pro Asp Arg Thr Leu Arg
            500                 505                 510
```

Leu Ala Leu Arg Pro Arg Thr Glu
        515                 520

<210> SEQ ID NO 6
<211> LENGTH: 1739
<212> TYPE: DNA
<213> ORGANISM: Drosophila

<400> SEQUENCE: 6

| | | | | | |
|---|---|---|---|---|---|
| cgttgctgtc | ggaatttgcc | gcgaaaagac | cagagtaacg | acgaaaaatg | ttgaccaaac | 60 |
| tgttaaagat | tagctgcacc | tcgaggcagt | gcacctttgc | caagccgtat | caggcgatac | 120 |
| caggaccacg | aggacccttt | ggaatgggta | atctatacaa | ttacctgccc | ggaatcggat | 180 |
| cctattcctg | gctaagattg | caccaagccg | gccaggataa | gtatgagaaa | tatgcgcaa | 240 |
| ttgtgcggga | aactatagtt | cctgggcagg | acattgtctg | gttgtacgat | cccaaggaca | 300 |
| tagctttgct | gctcaacgag | cgggattgtc | cgcagcgaag | aagtcacctg | gcactggctc | 360 |
| aatatcgcaa | gagccgaccg | gatgtctata | aaaccaccgg | cttgctgccc | accaatggtc | 420 |
| cggaatggtg | gcgtatacgt | gcccaggtgc | aaaaggagct | gagtgcacca | agagtgtgc | 480 |
| ggaacttcgt | tcgccaagtg | gatggagtga | ccaaggagtt | cattagattt | ctacaagaat | 540 |
| ctcgcaatgg | tggtgccatt | gatatgctgc | ccaagctcac | cagattgaat | ttggaattaa | 600 |
| cctctttgct | tacctttgga | gcccgtctgc | agtcttttac | tgcccaggaa | caagatccta | 660 |
| gttcccgatc | cactcgcttg | atggatgcgc | ccgagaccac | caatagctgc | atcctgccca | 720 |
| cagatcaggg | cctccagctg | tggcgatttc | tggagacacc | tagctttcgc | aaactaagcc | 780 |
| aggcccaatc | atatatggag | ggtgtggcca | tggagttagt | ggaggagaat | gttaggaatg | 840 |
| gttcagtggg | atcttcactg | atctcggctt | atgtaaaaaa | tcccgagctt | gatcgcagtg | 900 |
| acgtggtggg | caccgctgca | gatttactct | tggctggcat | cgataccact | tcgtatgcct | 960 |
| cggcatttct | gctctatcac | atagctcgaa | atccggaggt | gcagcaaaaa | ctgcacgagg | 1020 |
| aggccaagag | agtgcttccg | agtgccaagg | acgagctatc | catggatgcc | ctacgaactg | 1080 |
| atatcaccta | tacgagggct | gtcctcaagg | aatcactacg | cttgaatccc | attgccgtgg | 1140 |
| gcgtgggcag | gattcttaat | caggatgcga | tcttcagtgg | ctacttcgtg | ccaaaggga | 1200 |
| ccaccgtggt | tacccagaac | atggtacgct | gccggctgga | gcagcacttc | caggatcccc | 1260 |
| tgcgcttcca | accagatcga | tggctccagc | accgtagtgc | cctcaatccc | tatctggtcc | 1320 |
| ttcccttcgg | tcacggaatg | cgggcctgca | ttgcccgccg | tttggccgag | cagaaatatgc | 1380 |
| acattttgct | tctcaggctg | ctgcgtgaat | acgaattgat | ttggagcgga | tccgatgatg | 1440 |
| agatgggtgt | gaagaccctg | ttgataaata | aacccgatgc | tccagtgctg | atcgatctgc | 1500 |
| gattgcgtag | agaataaggt | tattaggtat | aagtaagtcg | ccagagcctt | aagactgaga | 1560 |
| tactagactc | gtgtcacgtt | taaataattc | gtttattaat | tatttaaat | tagctcataa | 1620 |
| ttaattataa | ttagtgtaaa | ttatatataa | ctagacttgc | attttatgtg | attgaaaggc | 1680 |
| tgtgggtgtt | ttggtctaag | tactaaagag | aacgactaaa | aggcaaaaaa | aaaaaaaaa | 1739 |

<210> SEQ ID NO 7
<211> LENGTH: 1725
<212> TYPE: DNA
<213> ORGANISM: Drosophila

<400> SEQUENCE: 7

| | | | | | |
|---|---|---|---|---|---|
| atgtcggcgg | acatcgtcga | tattggccac | accggttgga | tgcctcggt | gcagagcctg | 60 |

-continued

```
agtattctgc tggttccggg tgcgctcgtc ctggtgattc tctacctgtg cgagcgccag    120
tgcaatgacc tcatgggtgc cccaccgccg ggtccctggg gcctgcccct tctgggttac    180
ctgcccttcc tggacgcccg tgcgccgcac aagtcactcc agaagctggc caagcggtat    240
ggtggaattt tcgagctgaa aatgggcagg gtgccgaccg tagtcctctc ggatgccgcc    300
ttggtgcggg atttctttcg gcgcgatgtg atgactggcc gtgcgccgct ctacctcacc    360
cacggcatca tgggtggatt tggcatcatc tgcgcccagg aggacatttg gcgacatgca    420
cggcgcgaga ctatcgattg gctaaaggcc ttgggcatga cccgtcggcc ggggaactg     480 cgcgcgcggc tggagcggcg catagcccgc ggagtcgacg agtgcgtacg gcttttcgat    540
actgaggcaa agaagagctg tgcgtcggaa gtgaatccgc tgccggcgct ccatcactcg    600
ctgggcaaca taatcaacga cctggtcttc gggatcacct acaagcgcga cgaccccgac    660
tggctgtacc tgcagcggct gcaggaggag ggcgtcaagc tgattggcgt ctccggggtg    720
gtcaactttt tgccctggct gcgtcacctg cccgccaacg tgcgcaacat ccgcttcctg    780
ctggagggca aggccaagac gcacgccatc tacgaccgca ttgtggaggc ctgtggccag    840
cggctgaagg agaagcagaa ggtgttcaag gagctccagg agcagaagcg gctgcaaagg    900
cagctagaga aggagcagct caggcagtca aggaagcgg atccaagcca ggagcagagt     960
gaggcagacg aggatgacga ggagagcgat gaggaggaca cgtacgagcc ggagtgcatc   1020
ctggagcact tcctagccgt tcgagacacg gattcgcagc tctactgcga cgaccagctg   1080
cgccatctgc tggccgatct ctttggagcc ggggtggaca cctcgctggc caccctgcgc   1140
tggttcctgc tctacttggc ccgcgaacaa cgctgccagc ggcgcctgca tgagctcctc   1200
ctgccgctgg gtccgtctcc cactttggag gaactggagc cgctggccta cctaagggct   1260
tgcatttccg agacgatgcg catacgcagc gttgtcccac tgggcattcc gcacggatgc   1320
aaagagaact tcgtcgtggg cgattatttt atcaagggtg gttcgatgat cgtttgctcg   1380
gagtgggcta ccacatggac cccagtggcc ttcccggaac cggaggagtt ccgtccggag   1440
cgcttcttga ccgccgatgg agcctaccag gcgccgccac agttcatccc attctcgtcc   1500
ggctatcgaa tgtgtcccgg cgaagagatg gctcgcatga tactcacgct ctttacgggt   1560
cgcatcctca ggcgcttcca cttggaactg ccctcgggca ctgaggtgga catggcgggt   1620
gagagcggca tcaccctgac ccccactccg cacatgctgc gattcaccaa gctgccggcg   1680
gtggagatgc gccatgcacc cgacggagct gtggtgcagg attag                   1725
```

```
<210> SEQ ID NO 8
<211> LENGTH: 2164
<212> TYPE: DNA
<213> ORGANISM: Drosophila

<400> SEQUENCE: 8
```

```
agttgtgttt tgtgcttcct actttcaaga gctcagcaaa aatgctggct gctttgattt    60
acactatttt ggcgatttta ctgagtgttc tggccacgtc ctacatatgc attatatatg    120
gagtcaagcg ccgcgttctg cagcccgtta aaacaaagaa ttcaaccgaa atcaatcaca    180
atgcttatca aaatatacc caggctccag gaccacgacc atggcccatc attggtaatc    240
ttcatctgct ggatcgatac agggatagtc cctttgcggg attcacggcg ttggcacagc    300
aatacggaga catatactcc ctgaccttcg gacacacccg ctgtctggtg gtgaacaact    360
tggagctgat ccgcgaggtg ctcaatcaaa atggcaaggt gatgagcggg cggccagact    420
```

-continued

```
tcatacgata tcataaacta tttggtggcg agcgaagcaa ttcgttggct ctgtgcgatt      480
ggtcacagct gcagcagaag agaaggaatc tggccaggcg tcactgctcg cccagggaat      540
cttcctgctt ctacatgaaa atgtcccaga ttggttgcga ggaaatggag cactggaatc      600
gggagctggg aaaccaactc gttcctggag agccgatcaa catcaagcat ctgattctga      660
aggcctgtgc aaatatgttt agtcagtaca tgtgttcgtt gaggttcgac tacgatgatg      720
tggacttcca acagattgtt caatacttcg atgagatatt ctgggaaatc aatcagggac      780
atccgctgga ttttctaccc tggctatatc ccttctacca gcgacacctg aacaagatca      840
tcaactggtc ctcgactatc aggggattca taatggaaag gattatccgg catcgggagc      900
tgagcgtcga tttggatgaa ccagatcggg acttcacaga tgctctactt aaaagcctgc      960
ttgaagataa agatgtctcc cggaacacga ttatcttcat gctggaggat ttcattggtg     1020
gacattcagc ggttggaaat ctagtaatgc tagtgctggc ctatatagcc aaaaatgtgg     1080
atattggaag gagaatacaa gaggaaattg acgcaattac tgaagagaaa aataggtcaa     1140
ttaatttgct ggacatgaat gctatgccct acacgatggc gacgattttc gaggtgctgc     1200
gatattcatc ctccccaatt gttccacatg tggccaccga ggacacagtg atctctggct     1260
atgggtaac  caagggcacc attgtgttca tcaacaatta tgtgctaaac accagcgaga     1320
aattctgggt aaatcccaag gaatttaatc cattaagatt tttggaaccg tcaaaggaac     1380
aaagcccaaa aaattccaaa ggttctgatt ctggcatcga agtgataat gaaaaacttc      1440
aactaaagag gaatattccg cactttctgc cctttagcat cgggaagcgg acttgcatcg     1500
gccagaattt ggtgagagga tttggttttc tggtcgtggt caacgtaatg cagagatata     1560
atatcagcag tcataatcct tcgacgatta agatcagtcc ggagagtttg gcactgcctg     1620
ccgattgttt tccattggtc ttgacaccca gggaaaagat cggaccacta ataaaatta      1680
taaattaaaa accaatacca ttaagcacta gcaattaaaa tattacacat aaatagccca     1740
aacagcttca gaataagatt actgcgttat ctattatcag acataacgaa taagctcaat     1800
caaatagtaa aactatttta ctgttgagta tattttcaat tacttaacgc aaatacaaaa     1860
tttttgtatt tcatgtctat attttgtacg ataccaaaca cgcaaagtct tatagatgct     1920
caccacacta taaaaatttc acatacattc gattcttgag gatcttagga ttagattaat     1980
tcgttaagaa cttcgttaca gtaaatgact caaatatgta taatgtgcac gccgaatgta     2040
aattcaagtg taattcttaa gcgaaatatt tacaatttt attttctttt agaaatcaat     2100
aaatgtgggc ccagatgggc cttatataaa tgacatagaa acctaaagct gaataaatcg     2160
aaaa                                                                 2164
```

<210> SEQ ID NO 9
<211> LENGTH: 1623
<212> TYPE: DNA
<213> ORGANISM: Drosophila

<400> SEQUENCE: 9

```
atggccgtga tactgttgct ggccctggca ctcgtacttg tctgctactg cgctctccat       60
cggcacaaat tggcggatat ctacctccgg ccgctcctga agaacacgct ccttgaggac      120
ttctaccatg ccgagctgat ccagcccgag gcgccaaaga gcggaggcg cggcatctgg       180
gacatacccg ggccaaagag gattcccttc ctgggcacta gtggatatt cctgctcttc       240
tttcgacggt acaagatgac caagctgcac gaggtatatg cggatttgaa cagacaatat      300
ggggacatag tgctggaggt gatgccctcc aatgtgccaa tagtgcacct gtacaatcgc      360
```

-continued

```
gatgatctgg agaaggtgct gaagtacccc agcaaatacc cattccgacc tcccaccgag    420
atcatcgtga tgtaccgtca gtcccgaccg gatcgctatg caagtgttgg aattgtgaat    480
gagcaaggac caatgtggca cgcctacga tcttccctga cctccagcat tacttctccc     540
cgggtcctgc agaatttcct gccagccttg aatgcggttt gtgatgattt taccgaacta    600
ctgcgagcca ggcgggatcc ggatacactg gtggttccca atttcgaaga gctgccaat    660 ctgatgggtc tggaagctgt gtgcacttta atgctgggca gaaggatggg tttcctggct    720
atcgatacca gcagccgca aaagataagc caactggcag ctgctgttaa acagttttc     780 atatcccaaa gggactcgta ctacggtctg gtctgtgga aatactttcc caccaaaacg    840
tacagagact tgcccgcgc cgaggacttg atctatgatg tgatctccga gatcatcgat    900
catgagctgg aggaactcaa aaagtcggct gcctgcgagg atgacgaggc tgctggatta    960
cgaagtatct ttctgaatat tctggagctc aaggatctgg atatcaggga caaaaagtca   1020
gcgatcatag actttattgc cgctggcata gaaacgttag ccaacacttt gttgtttgta   1080
ctgagttctg ttactggaga tcccggtgct atgccacgaa tcctaagtga attctgcgag   1140
tatcgggaca cgaatatcct gcaggatgca ctaacgaatg ccacatacac aaaggcctgt   1200
atacaggagt cctacagact gaggcccaca gccttttgcc tggccagaat cctggaggag   1260
gacatggagc tctcgggcta ctcgcttaat gcagggactg tggtgctctg tcagaatatg   1320
atagcctgcc acaaggacag caacttccaa ggggccaagc agtttacccc agagcgttgg   1380
attgatcctg ccacggagaa tttcacggtg aacgtggata atgccagtat tgtggtgccc   1440
ttcggagtgg gtcgaagatc gtgtccagga aagcgttttg tggaaatgga ggtggtgctg   1500
ctgctagcta agatggtcct agcctttgat gtgagctttg tgaagccact ggaaacggag   1560
ttcgagttcc tgctggcacc caaaactcca ctcagtctaa gactcagcga tcgggttttc   1620
tga                                                               1623
```

<210> SEQ ID NO 10
<211> LENGTH: 1213
<212> TYPE: DNA
<213> ORGANISM: Drosophila

<400> SEQUENCE: 10

```
gcgcggagtc ttccagcacg agggtcagta tccgcagcat ccgctgccgg atgcctggac     60
gctgtataac cagcaacatg cctgccaacg gggactgttc ttcatggagg cgccgagtg    120 gctgcacaac cgacgcatac ttaatcgact gctgctcaac ggaaatttga attggatgga    180
cgtgcatatt gagagctgta ccagacgaat ggtggatcag tggaaaagac gcactgcgga    240
ggcggcggcg attccgctag cggagagtgg tgaaatacga agctacgaac tgccctgtt    300 ggaacaacag ctctaccgtt ggtccataga agttctgtgc tgcatcatgt ttggcaccag    360
cgtgctcacc tgccccaaga tccagtcctc gctggactac ttcacgcaga ttgtgcacaa    420
ggtgtttgag catagctcgc gactgatgac attcccgcct cgcttggccc agattttgcg    480
cctgcccatc tggcgggatt tcgaggccaa tgtggatgag gtgctgcgtg agggagctgc    540
cataatcgat cactgcatca gagtgcagga ggaccaaagg agaccgcacg atgaggcgct    600 taccatcgc ctccaggcgg cggatgtgcc aggcgatatg atcaagcgga tatttgtaga    660
cttggtcatt gcagcaggtg acacgaccgc attcagcagt cagtgggctt tgtttgccct    720
ttcaaaggag ccgaggctcc agcaacgact ggccaaggag cgagctacca atgattctcg    780
```

```
cctgatgcac ggcctgatca aggagtccct gcgtctgtac cccgtagctc ccttcattgg    840
ccgatatctg ccgcaggacg cgcaacttgg cggtcacttt atcgaaaagg ataccatggt    900
gctgctctcc ttgtacacgg caggtcgcga tccatcacac tttgagcagc cggaacgtgt    960
gctcccggag cgctggtgca ttggagagac ggagcaggtg cataagtcac acggcagtct   1020 gcctttttgcc atcggccagc ggtcttgcat tggtcgccgt gtggcactca agcagctcca   1080
ctccctgctg ggccgatgtg ctgctcagtt tgagatgagc tgccttaacg agatgcccgt   1140
tgacagcgta ctccgcatgg tcaccgtgcc cgatcggact ttgcgtttag cccttcggcc   1200
gcgaaccgag tga                                                      1213
```

```
<210> SEQ ID NO 11
<211> LENGTH: 10
<212> TYPE: PRT
<213> ORGANISM: Artificial Sequence
<220> FEATURE:
<223> OTHER INFORMATION: P450 motif
<220> FEATURE:
<221> NAME/KEY: VARIANT
<222> LOCATION: 2,3,5,6,7,9
<223> OTHER INFORMATION: Xaa = Any Amino Acid

<400> SEQUENCE: 11

Phe Xaa Xaa Gly Xaa Xaa Xaa Cys Xaa Gly
 1               5                  10

<210> SEQ ID NO 12
<211> LENGTH: 5
<212> TYPE: PRT
<213> ORGANISM: Artificial Sequence
<220> FEATURE:
<223> OTHER INFORMATION: heme binding motif
<220> FEATURE:
<221> NAME/KEY: VARIANT
<222> LOCATION: 2
<223> OTHER INFORMATION: Xaa = Ala or Gly
<220> FEATURE:
<221> NAME/KEY: VARIANT
<222> LOCATION: 3
<223> OTHER INFORMATION: Xaa = Any Amino Acid
<220> FEATURE:
<221> NAME/KEY: VARIANT
<222> LOCATION: 4
<223> OTHER INFORMATION: Xaa = Glu or Asp

<400> SEQUENCE: 12

Ala Xaa Xaa Xaa Thr
 1               5

<210> SEQ ID NO 13
<211> LENGTH: 4
<212> TYPE: PRT
<213> ORGANISM: Artificial Sequence
<220> FEATURE:
<223> OTHER INFORMATION: heme binding motif
<220> FEATURE:
<221> NAME/KEY: VARIANT
<222> LOCATION: 2,3
<223> OTHER INFORMATION: Xaa = Any Amino Acid

<400> SEQUENCE: 13

Glu Xaa Xaa Arg
 1

<210> SEQ ID NO 14
<211> LENGTH: 468
<212> TYPE: PRT
```

<213> ORGANISM: Drosophila

<400> SEQUENCE: 14

```
Met Leu Thr Lys Leu Leu Lys Ile Ser Cys Thr Ser Arg Gln Cys Thr
 1               5                  10                  15

Phe Ala Lys Pro Tyr Gln Ala Ile Pro Gly Pro Arg Gly Met Gly Asn
            20                  25                  30

Leu Tyr Asn Tyr Leu Pro Gly Ile Gly Ser Tyr Ser Trp Leu Arg Leu
        35                  40                  45

His Gln Ala Gly Gln Asp Lys Tyr Glu Lys Tyr Gly Ala Ile Val Arg
    50                  55                  60

Glu Thr Ile Val Pro Gly Gln Asp Ile Val Trp Leu Tyr Asp Pro Lys
65                  70                  75                  80

Asp Ile Ala Leu Leu Asn Glu Arg Asp Cys Pro Gln Arg Arg Ser
                85                  90                  95

His Leu Ala Leu Ala Gln Tyr Arg Lys Ser Arg Pro Asp Val Tyr Lys
            100                 105                 110

Thr Thr Gly Leu Leu Pro Thr Asn Gly Pro Glu Trp Trp Arg Ile Arg
        115                 120                 125

Ala Gln Val Gln Lys Glu Leu Ser Ala Pro Lys Ser Val Arg Asn Phe
    130                 135                 140

Val Arg Gln Val Asp Gly Val Thr Lys Glu Phe Ile Arg Phe Leu Gln
145                 150                 155                 160

Glu Ser Gly Ala Ile Asp Met Leu Pro Lys Leu Thr Arg Leu Asn Leu
                165                 170                 175

Glu Leu Thr Ser Leu Leu Thr Phe Gly Ala Arg Leu Gln Ser Phe Thr
            180                 185                 190

Ala Gln Glu Gln Asp Pro Ser Ser Thr Arg Leu Met Asp Ala Ala
    195                 200                 205

Glu Thr Thr Asn Ser Cys Ile Leu Pro Thr Asp Gln Gly Leu Gln Leu
    210                 215                 220

Trp Arg Thr Pro Ser Phe Arg Lys Leu Ser Gln Ala Gln Ser Tyr Met
225                 230                 235                 240

Glu Gly Val Ala Met Glu Leu Val Glu Glu Asn Val Arg Asn Gly Ser
                245                 250                 255

Val Gly Ser Ser Leu Ile Ser Ala Tyr Val Lys Asn Pro Glu Leu Asp
            260                 265                 270

Arg Ser Asp Val Val Gly Thr Ala Ala Asp Leu Leu Ala Gly Ile
    275                 280                 285

Asp Tyr Ala Ser Ala Phe Leu Leu Tyr His Ile Ala Arg Asn Pro Glu
290                 295                 300

Val Gln Gln Lys Leu His Glu Glu Ala Lys Arg Val Leu Pro Ser Ala
305                 310                 315                 320

Lys Asp Glu Leu Ser Met Asp Ala Leu Thr Asp Ile Thr Tyr Thr Arg
                325                 330                 335

Ala Val Leu Lys Glu Ser Leu Arg Leu Asn Pro Ile Ala Val Gly Val
            340                 345                 350

Gly Arg Ile Leu Asn Gln Asp Ala Ile Phe Ser Gly Tyr Phe Val Pro
        355                 360                 365

Thr Val Val Thr Gln Asn Met Val Arg Cys Arg Leu Glu Gln His Phe
    370                 375                 380

Gln Asp Pro Leu Arg Phe Gln Pro Asp Arg Trp Leu Gln His Arg Ser
385                 390                 395                 400
```

```
Ala Leu Asn Pro Tyr Leu Val Leu Pro Phe Gly His Gly Met Arg Ala
                405                 410                 415

Cys Ile Ala Arg Arg Leu Ala Glu Gln Asn Met Leu Leu Arg Leu Leu
            420                 425                 430

Arg Glu Tyr Glu Leu Ile Trp Ser Gly Ser Asp Asp Glu Met Gly Val
        435                 440                 445

Lys Thr Leu Leu Ile Asn Lys Pro Asp Ala Pro Val Leu Ile Asp Leu
450                 455                 460

Leu Arg Arg Glu
465

<210> SEQ ID NO 15
<211> LENGTH: 524
<212> TYPE: PRT
<213> ORGANISM: Drosophila

<400> SEQUENCE: 15

Met Leu Ala Ala Leu Ile Tyr Thr Ile Leu Ala Ile Leu Leu Ser Val
 1               5                  10                  15

Leu Ala Thr Ser Tyr Ile Cys Ile Ile Tyr Gly Val Lys Arg Arg Val
             20                  25                  30

Leu Gln Pro Val Lys Thr Lys Asn Ser Thr Glu Ile Asn His Asn Ala
         35                  40                  45

Tyr Gln Lys Tyr Thr Gln Ala Pro Gly Pro Arg Pro Ile Ile Gly Asn
     50                  55                  60

Leu His Leu Leu Asp Arg Tyr Arg Asp Ser Pro Phe Ala Gly Phe Thr
 65                  70                  75                  80

Ala Leu Ala Gln Gln Tyr Gly Asp Ile Tyr Ser Leu Thr Phe Gly His
                 85                  90                  95

Thr Arg Cys Leu Val Val Asn Asn Leu Glu Leu Ile Arg Glu Val Leu
            100                 105                 110

Asn Gln Asn Gly Lys Val Met Ser Gly Arg Pro Asp Phe Ile Arg Tyr
        115                 120                 125

His Leu Phe Gly Gly Glu Arg Ser Asn Ser Leu Ala Leu Cys Asp Trp
    130                 135                 140

Ser Gln Leu Gln Gln Lys Arg Arg Asn Leu Ala Arg Arg His Cys Ser
145                 150                 155                 160

Pro Arg Glu Ser Ser Cys Phe Tyr Met Lys Met Ser Gln Ile Gly Cys
                165                 170                 175

Glu Glu Met Glu His Trp Asn Arg Glu Leu Leu Val Pro Gly Glu Pro
            180                 185                 190

Ile Asn Ile Lys His Leu Ile Leu Lys Ala Cys Ala Asn Met Phe Ser
        195                 200                 205

Gln Tyr Met Cys Ser Leu Arg Phe Asp Tyr Asp Val Asp Phe Gln
    210                 215                 220

Gln Ile Val Gln Tyr Phe Asp Glu Ile Phe Trp Glu Ile Asn Gln Gly
225                 230                 235                 240

His Pro Leu Asp Phe Leu Pro Trp Leu Tyr Pro Arg His Leu Asn Lys
                245                 250                 255

Ile Ile Asn Trp Ser Ser Thr Ile Arg Gly Phe Ile Met Glu Arg Ile
            260                 265                 270

Ile Arg His Arg Glu Leu Ser Val Asp Leu Asp Glu Pro Asp Arg Asp
        275                 280                 285

Phe Thr Asp Ala Leu Leu Lys Ser Leu Leu Glu Asp Lys Asp Val Ser
    290                 295                 300
```

-continued

```
Arg Asn Thr Ile Ile Phe Met Leu Glu Asp Phe Ile Gly Gly His Ser
305                 310                 315                 320

Asn Leu Val Met Leu Val Leu Ala Tyr Ile Ala Lys Asn Val Asp Ile
                325                 330                 335

Gly Arg Arg Ile Gln Glu Ile Asp Ala Ile Thr Glu Glu Lys Asn
                340                 345                 350

Arg Ser Ile Asn Leu Leu Asp Met Asn Ala Met Pro Tyr Thr Met Ala
            355                 360                 365

Thr Ile Phe Glu Val Leu Arg Tyr Ser Ser Pro Ile Val Pro His
    370                 375                 380

Val Ala Thr Glu Asp Thr Val Ile Ser Gly Tyr Gly Val Thr Ile Val
385                 390                 395                 400

Phe Ile Asn Asn Tyr Val Leu Asn Thr Ser Glu Lys Phe Trp Val Asn
                405                 410                 415

Pro Lys Glu Phe Asn Pro Leu Arg Phe Leu Glu Pro Ser Lys Glu Gln
                420                 425                 430

Ser Pro Lys Asn Ser Lys Gly Ser Asp Ser Gly Ile Glu Ser Asp Asn
            435                 440                 445

Glu Lys Leu Gln Leu Lys Arg Asn Ile Pro His Phe Leu Pro Phe Ser
    450                 455                 460

Ile Lys Arg Thr Cys Ile Gly Gln Asn Leu Val Arg Gly Phe Gly Val
465                 470                 475                 480

Val Asn Val Met Gln Arg Tyr Asn Ile Ser Ser His Asn Pro Ser Thr
                485                 490                 495

Ile Lys Ile Ser Pro Glu Ser Leu Ala Leu Pro Ala Asp Cys Phe Pro
            500                 505                 510

Leu Val Leu Thr Pro Arg Glu Lys Ile Gly Pro Leu
            515                 520

<210> SEQ ID NO 16
<211> LENGTH: 552
<212> TYPE: PRT
<213> ORGANISM: Drosophila

<400> SEQUENCE: 16

Met Ser Ala Asp Ile Val Asp Ile Gly His Thr Gly Trp Met Pro Ser
1               5                   10                  15

Val Gln Ser Leu Ser Ile Leu Leu Val Pro Gly Ala Leu Val Leu Val
                20                  25                  30

Ile Leu Tyr Leu Cys Glu Arg Gln Cys Asn Asp Leu Met Gly Ala Pro
            35                  40                  45

Pro Pro Gly Leu Pro Phe Leu Gly Tyr Leu Pro Phe Leu Asp Ala Arg
        50                  55                  60

Ala Pro His Lys Ser Leu Gln Lys Leu Ala Lys Arg Tyr Gly Gly Ile
65                  70                  75                  80

Phe Glu Leu Lys Met Gly Arg Val Pro Thr Val Val Leu Ser Asp Ala
                85                  90                  95

Ala Leu Val Arg Asp Phe Arg Asp Val Met Thr Gly Arg Ala
                100                 105                 110

Pro Leu Tyr Leu Thr His Gly Ile Met Gly Gly Phe Gly Ile Ile Cys
            115                 120                 125

Asp Ile Trp Arg His Ala Arg Arg Glu Thr Ile Asp Trp Leu Lys Ala
130                 135                 140

Leu Gly Met Thr Arg Arg Pro Gly Glu Leu Arg Ala Arg Leu Glu Arg
```

```
            145                 150                 155                 160
    Arg Ile Arg Gly Val Asp Glu Cys Val Arg Leu Phe Asp Thr Glu
                    165                 170                 175
    Ala Lys Lys Ser Cys Ala Ser Glu Val Asn Pro Leu Pro Ala Leu His
                    180                 185                 190
    His Ser Leu Gly Asn Ile Ile Asn Asp Leu Val Phe Gly Ile Thr Tyr
                    195                 200                 205
    Lys Arg Asp Trp Leu Tyr Leu Gln Arg Leu Gln Glu Glu Gly Val Lys
                    210                 215                 220
    Leu Ile Gly Val Ser Gly Val Val Asn Phe Leu Pro Trp Leu Arg His
    225                 230                 235                 240
    Leu Pro Ala Asn Val Arg Asn Ile Arg Phe Leu Leu Glu Gly Lys Ala
                    245                 250                 255
    Lys Thr His Ala Ile Tyr Asp Arg Ile Val Glu Ala Cys Gly Gln Arg
                    260                 265                 270
    Leu Lys Glu Lys Lys Val Phe Lys Glu Leu Gln Glu Gln Lys Arg Leu
                    275                 280                 285
    Gln Arg Lys Glu Gln Leu Arg Gln Ser Lys Glu Ala Asp Pro Ser Gln
    290                 295                 300
    Glu Gln Ser Glu Ala Asp Glu Asp Glu Glu Ser Asp Glu Glu Asp
    305                 310                 315                 320
    Thr Tyr Glu Pro Glu Cys Ile Leu Glu His Phe Leu Ala Val Arg Asp
                    325                 330                 335
    Thr Asp Ser Gln Leu Tyr Cys Asp Asp Gln Leu Arg His Leu Leu Ala
                    340                 345                 350
    Asp Leu Phe Gly Ala Gly Val Asp Ala Thr Leu Arg Trp Phe Leu Leu
                    355                 360                 365
    Tyr Leu Ala Arg Glu Gln Arg Cys Gln Arg Arg Leu His Glu Leu Leu
                    370                 375                 380
    Leu Pro Leu Gly Pro Ser Pro Thr Leu Glu Glu Leu Glu Pro Leu Ala
    385                 390                 395                 400
    Tyr Leu Arg Ala Cys Ile Ser Glu Thr Met Arg Ile Arg Ser Val Val
                    405                 410                 415
    Pro Leu Gly Ile Pro His Gly Cys Lys Glu Asn Phe Val Val Gly Asp
                    420                 425                 430
    Tyr Phe Ile Lys Met Ile Val Cys Ser Glu Trp Ala Ile His Met Asp
                    435                 440                 445
    Pro Val Ala Phe Pro Glu Pro Glu Glu Phe Arg Pro Glu Arg Phe Leu
                    450                 455                 460
    Thr Ala Asp Gly Ala Tyr Gln Ala Pro Pro Gln Phe Ile Pro Phe Ser
    465                 470                 475                 480
    Ser Gly Tyr Arg Met Cys Pro Gly Glu Glu Met Ala Arg Met Ile Leu
                    485                 490                 495
    Thr Gly Arg Ile Leu Arg Arg Phe His Leu Glu Leu Pro Ser Gly Thr
                    500                 505                 510
    Glu Val Asp Met Ala Gly Glu Ser Gly Ile Thr Leu Thr Pro Thr Pro
                    515                 520                 525
    His Met Leu Arg Phe Thr Lys Leu Pro Ala Val Glu Met Arg His Ala
                    530                 535                 540
    Pro Asp Gly Ala Val Val Gln Asp
    545                 550

<210> SEQ ID NO 17
```

<211> LENGTH: 520
<212> TYPE: PRT
<213> ORGANISM: Drosophila

<400> SEQUENCE: 17

```
Met Ala Val Ile Leu Leu Ala Leu Ala Leu Val Leu Val Cys Tyr
 1               5                  10                  15

Cys Ala Leu His Arg His Lys Leu Ala Asp Ile Tyr Leu Arg Pro Leu
                20                  25                  30

Leu Lys Asn Thr Leu Leu Glu Asp Phe Tyr His Ala Glu Leu Ile Gln
            35                  40                  45

Pro Glu Ala Pro Lys Arg Arg Arg Gly Ile Trp Asp Ile Pro Gly
    50                  55                  60

Pro Lys Arg Ile Leu Gly Thr Lys Trp Ile Phe Leu Leu Phe Phe Arg
65                  70                  75                  80

Arg Tyr Lys Met Thr Lys Leu His Glu Val Tyr Ala Leu Asn Arg Gln
                85                  90                  95

Tyr Gly Asp Ile Val Leu Glu Val Met Pro Ser Asn Val Pro Ile Val
            100                 105                 110

His Leu Tyr Asn Arg Asp Asp Leu Glu Lys Val Leu Lys Tyr Pro Ser
        115                 120                 125

Lys Tyr Pro Phe Pro Pro Thr Glu Ile Ile Val Met Tyr Arg Gln Ser
    130                 135                 140

Arg Pro Asp Arg Tyr Ala Ser Val Gly Ile Val Asn Glu Gln Gly Pro
145                 150                 155                 160

Met Trp Gln Arg Leu Arg Ser Ser Leu Thr Ser Ser Ile Thr Ser Pro
                165                 170                 175

Arg Val Leu Gln Asn Phe Leu Pro Ala Leu Asn Ala Val Cys Asp Asp
            180                 185                 190

Phe Thr Glu Leu Leu Arg Ala Arg Asp Thr Leu Val Val Pro Asn Phe
        195                 200                 205

Glu Glu Leu Ala Asn Leu Met Gly Leu Ala Val Cys Thr Leu Met Leu
    210                 215                 220

Gly Arg Arg Met Gly Phe Leu Ala Ile Asp Thr Lys Gln Pro Gln Lys
225                 230                 235                 240

Ile Ser Gln Leu Ala Ala Val Lys Gln Leu Phe Ile Ser Gln Arg
                245                 250                 255

Asp Ser Tyr Tyr Gly Leu Gly Leu Trp Lys Thr Lys Thr Tyr Arg Asp
            260                 265                 270

Phe Ala Arg Ala Glu Asp Leu Ile Tyr Asp Val Ile Ser Glu Ile Ile
        275                 280                 285

Asp His Glu Leu Glu Leu Lys Lys Ser Ala Cys Glu Asp Asp
    290                 295                 300

Glu Ala Ala Gly Leu Arg Ser Ile Phe Leu Asn Ile Leu Glu Leu Lys
305                 310                 315                 320

Asp Leu Asp Ile Arg Asp Lys Lys Ser Ala Ile Ile Asp Phe Ile Ala
                325                 330                 335

Ala Gly Ile Glu Asn Thr Leu Leu Phe Val Leu Ser Ser Val Thr Gly
            340                 345                 350

Asp Pro Gly Ala Met Pro Arg Ile Leu Ser Glu Phe Cys Glu Tyr Arg
        355                 360                 365

Asp Thr Asn Ile Leu Gln Asp Ala Leu Thr Asn Ala Thr Tyr Thr Lys
    370                 375                 380

Ala Cys Ile Gln Glu Ser Tyr Arg Leu Arg Pro Thr Ala Phe Cys Leu
```

```
                385                 390                 395                 400
Ala Arg Ile Leu Glu Glu Asp Met Glu Leu Ser Gly Tyr Ser Leu Asn
                    405                 410                 415

Val Val Leu Cys Gln Asn Met Ile Ala Cys His Lys Asp Ser Asn Phe
                420                 425                 430

Gln Gly Ala Lys Gln Phe Thr Pro Glu Arg Trp Ile Asp Pro Ala Thr
            435                 440                 445

Glu Asn Phe Thr Val Asn Val Asp Asn Ala Ser Ile Val Val Pro Phe
        450                 455                 460

Gly Val Gly Arg Ser Cys Pro Gly Lys Arg Phe Val Glu Met Glu
465                 470                 475                 480

Val Leu Ala Lys Met Val Leu Ala Phe Asp Val Ser Phe Val Lys Pro
                485                 490                 495

Leu Glu Thr Glu Phe Glu Phe Leu Ala Pro Lys Thr Pro Leu Ser
                500                 505                 510

Leu Arg Leu Ser Asp Arg Val Phe
            515                 520

<210> SEQ ID NO 18
<211> LENGTH: 501
<212> TYPE: PRT
<213> ORGANISM: Drosophila

<400> SEQUENCE: 18

Met Thr Glu Lys Arg Glu Arg Pro Gly Pro Leu Arg Trp Leu Arg His
1               5                   10                  15

Leu Leu Asp Gln Leu Leu Val Arg Ile Leu Ser Leu Ser Leu Phe Arg
                20                  25                  30

Ser Arg Cys Asp Pro Pro Leu Gln Arg Phe Pro Ala Thr Glu Leu
            35                  40                  45

Pro Pro Ala Val Ala Ala Lys Tyr Val Pro Ile Pro Arg Val Leu Pro
        50                  55                  60

Val Val Gly Thr Leu Val Asp Leu Ile Ala Ala Gly Gly Ala Thr His
65                  70                  75                  80

Leu His Lys Tyr Ile Asp Ala Arg His Lys Gln Tyr Gly Pro Ile Phe
                85                  90                  95

Arg Glu Arg Leu Gly Gly Thr Gln Asp Ala Val Phe Val Ser Ser Ala
                    100                 105                 110

Asn Leu Met Arg Gly Val Phe Gln His Glu Gly Tyr Pro Gln His Pro
                115                 120                 125

Leu Pro Asp Ala Trp Thr Leu Tyr Asn Gln Gln His Ala Cys Gln Arg
        130                 135                 140

Gly Leu Phe Phe Met Glu Gly Ala Glu Trp Leu His Asn Arg Arg Ile
145                 150                 155                 160

Leu Asn Arg Leu Leu Asn Gly Asn Leu Asn Trp Met Asp Val His
                165                 170                 175

Ile Glu Ser Cys Thr Arg Arg Met Val Asp Gln Trp Lys Arg Arg Thr
                180                 185                 190

Ala Glu Ala Ala Ala Ile Pro Leu Ala Glu Ser Arg Ser Tyr Glu Leu
                195                 200                 205

Pro Leu Leu Glu Gln Gln Leu Tyr Arg Trp Ser Ile Glu Val Leu Cys
        210                 215                 220

Cys Ile Met Phe Gly Thr Ser Val Leu Thr Cys Pro Lys Ile Gln Ser
225                 230                 235                 240
```

-continued

```
Ser Leu Asp Tyr Phe Thr Gln Ile Val His Lys Val Phe Glu His Ser
            245                 250                 255

Ser Arg Leu Met Thr Phe Pro Pro Arg Leu Ala Gln Leu Pro Ile Trp
            260                 265                 270

Arg Asp Phe Glu Ala Asn Val Asp Glu Val Leu Arg Glu Gly Ala Ala
            275                 280                 285

Ile Ile Asp His Cys Ile Arg Val Gln Glu Asp Gln Arg Arg Pro His
            290                 295                 300

Asp Glu Ala Leu Tyr His Arg Leu Gln Ala Ala Asp Val Pro Gly Asp
305                 310                 315                 320

Met Ile Lys Arg Ile Phe Val Asp Leu Val Ile Ala Ala Gly Asp Phe
                325                 330                 335

Ser Ser Gln Trp Ala Leu Phe Ala Leu Ser Lys Glu Pro Arg Leu Gln
                340                 345                 350

Gln Arg Leu Ala Lys Glu Arg Ala Thr Asn Asp Ser Arg Leu Met His
            355                 360                 365

Gly Leu Ile Lys Glu Ser Leu Arg Leu Tyr Pro Val Ala Pro Phe Ile
            370                 375                 380

Gly Arg Tyr Leu Pro Gln Asp Ala Gln Leu Gly Gly His Phe Ile Glu
385                 390                 395                 400

Met Val Leu Leu Ser Leu Tyr Thr Ala Gly Arg Asp Pro Ser His Phe
                405                 410                 415

Glu Gln Pro Glu Arg Val Leu Pro Glu Arg Cys Ile Gly Glu Thr Glu
            420                 425                 430

Gln Val His Lys Ser His Gly Ser Leu Pro Phe Ala Ile Gly Gln Arg
            435                 440                 445

Ser Cys Ile Gly Arg Arg Val Ala Leu Lys Gln Leu Leu Gly Arg Cys
            450                 455                 460

Thr Ala Gln Phe Glu Met Ser Cys Leu Asn Glu Met Pro Val Asp Ser
465                 470                 475                 480

Val Leu Arg Met Val Thr Val Pro Asp Gln Thr Leu Arg Leu Ala Leu
                485                 490                 495

Arg Pro Arg Thr Glu
            500
```

METHODS FOR IDENTIFYING ECDYSTEROID SYNTHESIS INHIBITORS USING THE DROSOPHILA P450 ENZYME SHADE

CROSS REFERENCE TO RELATED APPLICATIONS

This application claims priority under 35 U.S.C. §119(e) of U.S. Application No. 60/318,006, filed Sep. 7, 2001, and U.S. Application No. 60/317,890, filed Sep. 7, 2001.

FEDERALLY SPONSORED RESEARCH

The U.S. Government may have certain rights in this invention pursuant to Grant No. IBN 9603710 awarded by The National Science Foundation, and Grant No. DK-30118 awarded by The National Institutes of Health.

TECHNICAL FIELD

The invention relates to methods and materials for identifying molecules that have insecticidal properties. In particular, the invention pertains to methods and materials for identifying molecules that inhibit ecdysteroid biosynthetic enzymes. The invention also pertains to transgenic organisms that express exogenous ecdysone biosynthetic enzymes.

BACKGROUND

Pest insects adversely affect agriculture production by decreasing crop yield and/or crop quality. One way to control pest insects involves disrupting metabolic functions that are vital to insect development and growth.

The ecdysteroids ecdysone ("ECD") and 20-hydroxyecdysone ("20E") play an important role in insect development. Ecdysteroid pulses regulate larval molts, larval and prepupal transitions, and differentiation of adult tissues during pupation. See e.g., Riddiford, L. M. (1993), Hormones and Drosophila Development, In *The Development of Drosophila melanogaster*, Vol. II (ed. M. Bate and A. Martinez Arias), pp. 899–939, Cold Spring Harbor, Cold Spring Harbor Press. Ecdysteroids also regulate oogenesis and patterning of the embryonic cuticle. See e.g., Buszczak et al. (1999) *Development* 126:4581–4589; Bender et al. (1997) *Cell* 91:777–788; Henrich et al. (1999) Peptide hormones, syteroid hormones and puffs: Mechanisms and models in insect development, In *Vitamins and Hormones* (ed. Litwack) Vol. 55, pp. 73–125, Academic Press, San Diego.

Insects cannot make the cyclopentanoperhydrophenanthrene structure of ecdysteroids de novo, and build ecdysteroids from dietary steroids (e.g., cholesterol and phytosteroids). Generally, biosynthesis of ECD and 20E from cholesterol involves a series of oxidation, reduction and hydroxylation steps. See e.g., Gilbert et al., *Control and Biochemical Nature of the Ecdysteroidogenic Pathway, Ann Rev Entomology* (in press). 20E is made from ECD.

While the ecdysteroid biosynthetic pathway and the effects of ECD and 20E on insect development are relatively well characterized, the identity of the genes and proteins involved in ecdysteroid biosynthesis is as yet largely unknown.

SUMMARY

The invention features methods and materials for identifying molecules that target the enzymes involved in ecdysone biosynthesis. The methods and materials of the invention can facilitate the discovery and manufacture of new insecticides.

In one aspect, the invention provides methods for identifying inhibitors of ecdysteroid synthesis. Such methods can include contacting an ecdysteroid biosynthetic enzyme with a candidate inhibitor molecule, and determining whether or not the molecule inhibits the activity of the enzyme. Typically, the enzyme has the amino acid sequence shown in SEQ ID NO:3, or an amino acid sequence substantially identical to the amino acid sequence of SEQ ID NO: 1, SEQ ID NO:2, SEQ ID NO:4, or SEQ ID NO:5.

Generally, the determining step uses a product-specific antibody or a substrate-specific antibody. A product-specific antibody can have specific binding affinity for a product such as ketotriol (2,22-dideoxyecdysone), ketodiol (2,22,25-trideoxyecdysone), diketol (3-dehydroketodiol), 2dE (2-deoxyecdysone), 22dE (22-deoxyecdysone), E (ecdysone), 20E (20-hydroxyecdysone), C (cholesterol), 25C (25-hydroxycholesterol), 7dC (7-dehydrocholesterol), 7d25C (7-dehydro-25-hydroxycholesterol), sitosterol, fucosterol, and stigmasterol. A substrate-specific antibody can have specific binding affinity for a substrate such as 22dE, 2dE, E, 20E, 26E (26-hydroxyecdysone), 20,26E (20, 26-dihydroxyecdysone), 7dC, 7d25C, "delta"-4-diketol, diketol, ketodiol, ketotriol, fucosterol, fucosterol epoxide stigmasterol epoxide and 5- and/or 11-hydroxyecdysteroids. Typically, the product-specific antibody or the substrate-specific antibody is attached to a solid substrate, and the solid substrate can be a microtiter plate.

In another aspect, the invention provides methods for determining whether or not a molecule has insecticidal properties. Such methods can include contacting an insect with a molecule that inhibits an ecdysteroid biosynthetic enzyme, and determining whether or not the molecule decreases the viability of the insect. Typically, the enzyme has the amino acid sequence shown in SEQ ID NO:3, or an amino acid sequence substantially identical to the amino acid sequence of SEQ ID NO:1, SEQ ID NO:2, SEQ ID NO:4, or SEQ ID NO:5.

In yet another aspect, the invention provides methods for making inhibitors of ecdysteroid synthesis. Such methods can include contacting an ecdysteroid biosynthetic enzyme with at least one candidate inhibitor molecule, determining whether or not the molecule inhibits the activity of the enzyme, and synthesizing a plurality of the molecules that inhibit the activity of the enzyme. Typically, the enzyme has the amino acid sequence shown in SEQ ID NO:3, or an amino acid sequence substantially identical to the amino acid sequence of SEQ ID NO:1, SEQ ID NO:2, SEQ ID NO:4, or SEQ ID NO:5.

In another aspect of the invention, there are provided methods for making an insecticide. Such methods can include contacting an insect with a molecule that inhibits the activity of an ecdysteroid biosynthetic enzyme, determining whether or not the molecule decreases the viability of the insect, and synthesizing a plurality of the molecules that decrease the viability of the insect. Typically, the enzyme has the amino acid sequence shown in SEQ ID NO:3, or an amino acid sequence substantially identical to the amino acid sequence of SEQ ID NO:1, SEQ ID NO:2, SEQ ID NO:4, or SEQ ID NO:5.

In still another aspect, the invention provides a kit for testing whether or not a molecule affects the activity of an ecdysteroid biosynthetic enzyme. A kit of the invention can include, separately or in association, one or more elements selected from the group consisting of the enzyme, a nucleic acid construct encoding the enzyme, and a host cell containing the enzyme, and one or more elements selected from the group consisting of a substrate of the enzyme, a product of the enzyme, a tracer, an antibody specific for the substrate, and an antibody specific for the product. Typically, the enzyme has the amino acid sequence shown in SEQ ID NO:3, or an amino acid sequence substantially identical to the amino acid sequence of SEQ ID NO:1, SEQ ID NO:2, SEQ ID NO:4, or SEQ ID NO:5.

In another aspect, the invention provides a transgenic plant that expresses an exogenous enzyme having the amino acid sequence shown in SEQ ID NO:3 or an exogenous enzyme having an amino acid sequence substantially identical to the amino acid sequence of SEQ ID NO:1, SEQ ID NO:2, SEQ ID NO:4, or SEQ ID NO:5. Representative plants can be selected from a genus such as *Anacardium, Arachis, Asparagus, Atropa, Avena, Brassica, Citrus, Citrullus, Capsicum, Carthamus, Cocos, Coffea, Cucumis, Cucurbita, Daucus, Elaeis, Fragaria, Glycine, Gossypium, Helianthus, Heterocallis, Hordeum, Hyoscyamus, Lactuca, Linum, Lolium, Lupinus, Lycopersicon, Malus, Manihot, Majorana, Medicago, Nicotiana, Olea, Oryza, Panicum, Pannesetum, Persea, Phaseolus, Pistachia, Pisum, Pyrus, Prunus, Raphanus, Ricinus, Secale, Senecio, Sinapis, Solanum, Sorghum, Theobromus, Trigonella, Triticum, Vicia, Vitis, Vigna* and *Zea*.

In another aspect, the invention provides an isolated polypeptide that includes an amino acid sequence substantially identical to SEQ ID NO: 1. Such a polypeptide can catalyze the conversion of 2,22-dideoxyecdysone to 2-deoxyecdysone. Generally, a *Drosophila* embryo lacking the activity of the polypeptide is non-viable, and a *Drosophila* organism having a reduced level of activity of the polypeptide produces reduced levels of ecdysteroids ecdysone (ECD) and 20-hydroxyecdysone (20E) relative to a wild-type *Drosophila* organism. Typically, such a polypeptide can functionally complement a *Drosophila* homozygous dib mutant. The invention further provides a host cell containing such a polypeptide. In addition, the invention provides an isolated nucleic acid consisting essentially of a nucleic acid having the sequence shown in SEQ ID NO:6, or the complement thereof. The invention additionally provides a nucleic acid construct comprising a nucleic acid having the sequence shown in SEQ ID NO:6, or the complement thereof.

In another aspect, the invention provides an isolated polypeptide that includes an amino acid sequence substantially identical to SEQ ID NO:2. Generally, a *Drosophila* embryo lacking the activity of the polypeptide is non-viable, and a *Drosophila* organism having a reduced level of activity of the polypeptide produces reduced levels of ecdysteroids ecdysone (ECD) and 20-hydroxyecdysone (20E) relative to a wild-type *Drosophila* organism. Typically, such a polypeptide can functionally complement a *Drosophila* homozygous phm mutant. The invention further provides a host cell containing such a polypeptide. In addition, the invention provides an isolated nucleic acid consisting essentially of a nucleic acid having the sequence shown in SEQ ID NO:7, or the complement thereof. The invention additionally provides a nucleic acid construct comprising a nucleic acid having the sequence shown in SEQ ID NO:7, or the complement thereof.

In yet another aspect, the invention provides an isolated polypeptide that includes the amino acid sequence shown in SEQ ID NO:3. Generally, a *Drosophila* embryo lacking the activity of the polypeptide is non-viable, and a *Drosophila* organism having a reduced level of activity of the polypeptide produces reduced levels of ecdysteroids ecdysone (ECD) and 20-hydroxyecdysone (20E) relative to a wild-type *Drosophila* organism. Typically, such a polypeptide can functionally complement a *Drosophila* homozygous spo mutant. The invention further provides a host cell containing such a polypeptide. In addition, the invention provides an isolated nucleic acid consisting essentially of a nucleic acid having the sequence shown in SEQ ID NO:8, or the complement thereof. The invention further provides a nucleic acid construct comprising a nucleic acid having the sequence shown in SEQ ID NO:8, or the complement thereof.

In another aspect, the invention provides an isolated polypeptide that includes an amino acid sequence substantially identical to SEQ ID NO:4. Generally, a *Drosophila* embryo lacking the activity of the polypeptide is non-viable, and a *Drosophila* organism having a reduced level of activity of the polypeptide produces reduced levels of ecdysteroids ecdysone (ECD) and 20-hydroxyecdysone (20E) relative to a wild-type *Drosophila* organism. Typically, such a polypeptide can functionally complement a *Drosophila* homozygous shd mutant. The invention further provides a host cell containing such a polypeptide. In addition, the invention provides an isolated nucleic acid consisting essentially of a nucleic acid having the sequence shown in SEQ ID NO:9, or the complement thereof. The invention additionally provides a nucleic acid construct comprising a nucleic acid having the sequence shown in SEQ ID NO:9, or the complement thereof.

In still another aspect, the invention provides an isolated polypeptide that includes an amino acid sequence substantially identical to SEQ ID NO:5. Such a polypeptide can catalyze the conversion of 2,22-dideoxyecdysone to 22-deoxyecdysone and/or 2-deoxyecdysone to ecdysone. Generally, a *Drosophila* embryo lacking the activity of the polypeptide is non-viable, and a *Drosophila* organism having a reduced level of activity of the polypeptide produces reduced levels of ecdysteroids ecdysone (ECD) and 20-hydroxyecdysone (20E) relative to a wild-type *Drosophila* organism. Typically, such a polypeptide can functionally complement a *Drosophila* homozygous sad mutant. The invention further provides a host cell containing such a polypeptide. In addition, the invention provides an isolated nucleic acid consisting essentially of a nucleic acid having the sequence shown in SEQ ID NO:10, or the complement thereof. The invention additionally provides a nucleic acid construct comprising a nucleic acid having the sequence shown in SEQ ID NO: 10, or the complement thereof.

Unless otherwise defined, all technical and scientific terms used herein have the same meaning as commonly understood by one of ordinary skill in the art to which this invention belongs. Although methods and materials similar or equivalent to those described herein can be used in the practice or testing of the present invention, suitable methods and materials are described below. In addition, the materials, methods, and examples are illustrative only and not intended to be limiting. All publications, patent applications, patents, and other references mentioned herein are incorporated by reference in their entirety. In case of conflict, the present specification, including definitions, will control.

The details of one or more embodiments of the invention are set forth in the accompanying drawings and the description below. Other features, objects, and advantages of the invention will be apparent from the drawings and detailed description, and from the claims.

DESCRIPTION OF DRAWINGS

FIG. 1 shows an alignment of novel P450 polypeptide sequences. DIB, SEQ ID NO:14; SPO, SEQ ID NO:16; PHM, SEQ ID NO:15; SHADE, SEQ ID NO:17; SHADOW, SEQ ID NO:18.

FIG. 2 shows the results of HPLC analysis of methanol extracts of the cells transfected with dib cDNA.

FIG. 3 shows the results of HPLC analysis of methanol extracts of the cells transfected with shadow cDNA.

DETAILED DESCRIPTION

The invention provides methods and materials for identifying inhibitors of enzymes involved in ecdysteroid biosynthesis. The invention is based, in part, on the discovery of novel ecdysteroid biosynthetic enzymes. Such enzymes can be used in screens to identify insecticidal molecules that target the ecdysone biosynthetic pathway. The invention also provides transgenic organisms that express exogenous ecdysteroid biosynthetic enzymes.

Novel Ecdysteroid Biosynthetic Enzymes

The products of the *Drosophila* disembodied (dib), spook (spo), shade (shd), shadow (sad), and phantom (phm) genes appear to be involved in a common developmental pathway. Mutations in each of these genes cause a very similar embryonic lethal phenotype: failure of cuticle differentiation; failure of head involution; abnormal gut morphogenesis and dorsal closure. The common defect in cuticle development suggests that dib, spo, shd, sad, and phm might encode enzymes involved, directly or indirectly, in ecdysteroid biosynthesis.

The products of dib, spo, shd, sad, and phm appear to be required for the synthesis of ECD and/or 20E. Mutations in dib, spo, shd, sad, and phm decrease or eliminate 20E-dependant transcription of the IMP-E1 gene in the embryonic epidermis. See Example 3. Biochemical analyses confirm that ECD and 20E levels are reduced at least 4-fold in heterozygous dib, spo, shd, sad, and phm mutants relative to wild type flies. See Example 4, Tables 1 & 2 (showing the effect of dib and spook mutations on ECD and 20E levels).

Enzymes that exhibit biochemical properties characteristic of cytochrome P450 enzymes reportedly catalyze at least four of the steps in the ECD and 20E biosynthetic pathways. See Grieneisen et al. (1993) *Insect Biochem. Mol. Biol.* 23:13–23. The dib, spo, shd, sad, and phm genes encode P450 enzymes. P450 sequences are located in the vicinity of the map locations of the dib, spo, shd, sad, and phm loci. Genomic DNA from wild type and one or more mutant strains corresponding to each of these P450 genes was sequenced. At least one mutant allele was identified for each P450 gene. An alignment of the dib, spo, shd, sad, and phm P450 gene products is presented in FIG. 1.

Cytochrome P450 enzymes are a highly diverse superfamily of heme-containing proteins. These proteins display an unusual reduced carbon monoxide difference spectrum that has an absorbance peak at 450 nm (hence Pigment at 450 m or "P450"). The characteristic spectrum is caused by a thiolate anion acting as the 5$^{th}$ ligand to the heme. P450 enzymes most commonly catalyze hydroxylation reactions, often of a lipophilic substrate. P450 proteins perform a wide spectrum of other reactions including N-oxidation, sulfoxidation, epoxidation, N-, S-, and O-dealkylation, peroxidation, deamination, desulfuration and dehalogenation.

More than 1500 P450 cytochrome sequences are known. Among P450 enzymes, the C-terminal half is more highly conserved than the N-terminal half. One P450 signature motif is the heme ligand, usually represented as FXXGXXXCXG (where "X" is any amino acid) (SEQ ID ID NO:12) where the Te residue is pat of the oxygen binding site. The K-helix has an invariant ENXR (SEQ ID NO:13) sequence that tolerates no substitutions.

The proteins encoded by dib, spo, shd, sad, and phm are less than 40% identical to P450 enzymes listed in public databases, and are, by the rules of the P450 Nomenclature Committee (see drnelson.utmem.edu/cytochromeP450.html on the World Wide Web founding members of novel P450 families. In accord with P450 Nomenclature Committee rules, the enzyme encoded by dib is designated CYP302a1, phm encodes CYP306a1, spo encodes CYP307a1, shd encodes CYP314a1, and sad encodes CYP315a1. The cDNA sequences for dib, spo, shd, sad, and phm and the amino acid sequences of the corresponding encoded proteins are shown in Table 3.

Nucleic acid molecules encoding each of the novel P450 enzymes were obtained from *Drosophila* embryonic cDNA libraries, cloned into expression vectors, and introduced into *Drosophila* S2 cells. Transfected cells were incubated with particular substrates for 2 to 24 hours and then harvested and extracted with methanol. Methanol extracts were analyzed by HPLC, and reaction products were identified based on their mobility characteristics relative to known standards. CYP302a1, encoded by dib, can catalyze the conversion of 2,22-dideoxyecdysone to 2-deoxyecdysone. See FIG. 2. CYP315a1, encoded by sad, can convert 2,22-dideoxy-ecdysone to 22-deoxyecdysone. See FIG. 3. CYP315a1 can also convert 2-deoxyecdysone to ecdysone. The spo, shd and phm genes appear to encode enzymes that catalyze earlier steps in the ecdysteroid biosynthetic pathway.

Methods and Materials for Identifying Inhibitors of Ecdysteroid Synthesis

In one aspect, the invention provides methods for identifying inhibitors of ecdysteroid synthesis. The methods involve contacting an ecdysteroid biosynthetic enzyme with a candidate inhibitor molecule and determining whether or not the molecule decreases the activity of the enzyme.

Ecdysteroid biosynthetic enzymes suitable for use in the invention include the CYP302a1 protein (SEQ ID NO:1), the CYP306a1 protein (SEQ ID NO:2), the CYP307a1 protein (SEQ ID NO:3), the CYP314a1 protein (SEQ ID NO:4), and the CYP315a1 protein (SEQ ID NO:5). In addition, ecdysteroid biosynthetic enzymes suitable for use in the invention include enzymes substantially identical to the CYP302a1 protein (SEQ ID NO: 1), the CYP306a1 protein (SEQ ID NO:2), the CYP314a1 protein (SEQ ID NO:4), and the CYP315a1 protein (SEQ ID NO:5). With respect to the CYP302a1 protein, "substantially identical" refers to proteins having at least 95% sequence identity to SEQ ID NO: 1. With respect to the CYP306a1 protein, "substantially identical" refers to proteins having at least 85% sequence identity to SEQ ID NO:2. With respect to the CYP314a1 protein, "substantially identical" refers to proteins having at least 98% sequence identity to SEQ ID NO:4. With respect to the CYP315a1 protein, "substantially identical" refers to proteins having at least 95% sequence identity to SEQ ID NO:5.

Suitable polypeptides that are substantially identical to the polypeptides having the amino acid sequence shown in SEQ ID NO:1, SEQ ID NO:2, SEQ ID NO:4, or SEQ ID NO:5 can have one or more amino acid substitutions, insertions or deletions relative to one of the above-identified P450 enzymes. Thus, suitable homologs can correspond to a part (e.g., a characteristic amino acid sequence element or functional domain) of one of the above-identified P450 enzymes. For use in the methods of the invention, the above-described ecdysteroid biosynthetic enzymes should possess functional activity to determine whether or not the enzyme is inhibited by a candidate inhibitor molecule. Non-functional ecdysteroid biosynthetic enzymes, however, also have utility. Non-functional ecdysteroid biosynthetic enzymes can be used, for example, to purify a substrate. A non-functional ecdysteroid biosynthetic enzyme also can be used as a candidate inhibitor molecule since such a molecule can compete with the wild-type enzyme for substrate binding but will not generate a product.

Suitable homologs typically have amino acid sequence elements characteristic of P450 enzymes. One characteristic P450 amino acid sequence element is the heme ligand, usually represented as FXXGXXXCXG (SEQ ID NO:11), which can tolerate exceptions at the three non-cysteine positions. The heme-binding region is typically about 50 amino acids from the C-terminal of the protein. Another characteristic P450 amino acid sequence element is the 1helix, which has a conserved motif A(A,G)X(E,D)T (SEQ ID NO: 12). The K-helix has an invariant EXXR (SEQ ID NO: 13) sequence that tolerates no substitutions. Other characteristic P450 sequence elements are described in Nelson, *Methods in Molecular Biology*. Vol. 107. Cytochrome P450 Protocols. eds. Phillips & Shephard. Humana Press, Totowa, N. J., pp. 15–24, 1998.

Suitable homologs of the above-identified P450 enzymes can be synthesized on the basis of amino acid sequence elements characteristic of the above-identified P450 enzymes. Suitable homologs can also be identified by homologous sequence analysis from a database of nucleotide or polypeptide sequences. For example, homologous sequence analysis can involve BLAST or PSI-BLAST analysis of databases using the amino acid sequences of the above-identified P450 enzymes. Potentially useful homologs also can be identified by manual inspection of candidates that appear to have amino acid sequence elements characteristic of the above-identified P450 enzymes.

A percent identity for any "target" nucleic acid or amino acid sequence relative to another "subject" nucleic acid or amino acid sequence (e.g.,, the nucleic acid or amino acid sequence of any of above-identified P450 enzymes) can be determined by using the BLAST 2 Sequences (B12seq) program from the stand-alone BLASTZ application (version 2.0.14) containing BLASTN and BLASTP. BLASTZ version 2.0.14 can be obtained at fr.com or at ncbi.nlm.nih.gov on the World Wide Web. Instructions explaining how to use BLASTZ, and specifically the B12seq program, can be found in the 'readme' file accompanying BLASTZ. The programs also are described in detail by Karlin et al, 1990, *Proc. Natl. Acad. Sci.*, 87:2264; Karlin et al, 1990, *Proc. Natl. Acad. Sci.*, 90:5873; and Altschul et al, 1997, *Nuci. Acids Res.*, 25:3389.

B12 seq performs a comparison between two sequences using either the BLASTN or BLASTP algorithm. BLASTN is used to compare nucleic acid sequences, while BLASTP is used to compare amino acid sequences. To compare two nucleic acid sequences, the options are set as follows: -i is set to a file containing the first nucleic acid sequence to be compared (e.g., C:\seq1.txt); -j is set to a file containing the second nucleic acid sequence to be compared (e.g., C:\seq2.txt); -p is set to blastn; -o is set to any desired file name (e.g., C:\output.txt); -q is set to −1; -r is set to 2; and all other options are left at their default setting. The following command can be used to generate an output file containing a comparison between two nucleic acid sequences: C:\B12seq-i c:\seq1.txt-j c:\seq2.txt -p blastn-o c:\output.txt-q-1-r 2. To compare two amino acid sequences, the options of B12 seq are set as follows: -i is set to a file containing the first amino acid sequence to be compared (e.g., C:\seq1.txt); -j is set to a file containing the second amino acid sequence to be compared (e.g., C:\seq2.txt); -p is set to blastp; -o is set to any desired file name (e.g., C:\output.txt); and all other options are left at their default setting. The following command can be used to generate an output file containing a comparison between two amino acid sequences: C:\B12 seq-i c:\seq1.txt-j c:\seq2.txt -p blastp-o c:\output.txt. If the two compared sequences share homology, then the designated output file will present those regions of homology as aligned sequences. If the two compared sequences do not share homology, then the designated output file will not present aligned sequences. Once aligned, the number of matches is determined by counting the number of positions where an identical nucleotide or amino acid residue is presented in both sequences.

The percent identity is determined by dividing the number of matches by the length of the subject sequence followed by multiplying the resulting value by 100. For example, if a target sequence is compared to a subject sequence having a length of 1000 and the number of matches is 900, then the sequence has a percent identity of 90% (i.e., 900÷1000× 100=90%) relative to the subject sequence.

Whether a homolog of one of the above-identified P450 enzymes is suitable for the invention can be readily determined by functional complementation. Functional complementation involves introducing a gene encoding a homolog into *Drosophila* homozygous for the dib, spo, shd, sad, or phm mutations indicated in FIG. 1. Homologs that increase the ecdysone titer in a statistically significant way relative to the appropriate homozygous mutant are useful for the invention. Ecdysone titers can be measured as described in Example 4.

Additional amino acid sequences (e.g., FLAG™ (U.S. Pat. No. 4,851,341); 6×HIS; c-myc; Protein C; VSV-G; Hemagglutinin; biotin; and GFP) can be attached to any one of the above-identified P450 enzymes or homologs to assist in, for example, purification of one or more of the above-identified P450 enzymes or homologs thereof.

In the methods of the invention, suitable ecdysteroid biosynthetic enzymes are brought into contact with a candidate inhibitor molecule. Any molecule can be a suitable candidate inhibitor molecule.

Suitable ecdysteroid biosynthetic enzymes and candidate inhibitor molecules are typically brought into contact with one another within a cell. Nucleic acid constructs encoding suitable ecdysteroid biosynthetic enzymes can be introduced into host cells (e.g., *Drosophila* S2 cells) by a variety of means, including liposome-mediated transfer, calcium phosphate co-precipitation, electroporation and DDAB-mediated transfection. See e.g., Trotter & Wood (1995) *Methods Molec. Biol.*, 39:97; Han (1996) *Nucleic Acid Res.*, 24:4362. Means for expressing recombinant proteins in insect cells are well known in the art. See e.g., O'Reilly et al. (1992) In: *Baculovirus Expression Vectors: A Laboratory Manual*, W. H. Freeman and Company, 216; Vaughn et al. (1977) *In Vitro*, 13:213. Exemplary transfer vectors for heterologous protein production are based upon *Autographa californica nuclear polyhedrosis virus* (AcNPV). The AcNPV viral genome is 134 kb in length and is functionally characterized by genes that are expressed early, late and very late during infection. See e.g., Ayres et al. (1994) *Virology,* 202:586; Friesen & Miller (1986) *In The Molecular Biology of Baculoviruses,* Springer-Verlag, Berlin, 31. In some embodiments, a host cell expresses only one ecdysteroid biosynthetic enzyme. In other embodiments, a host cell expresses other enzymes in the ecdysteroid biosynthetic pathway.

Enzyme and radio-immunoassays ("EIA" and "RIA") can be used to determine whether a candidate inhibitor molecule decreases the activity of an ecdysteroid biosynthetic enzyme. In one format ("Format 1"), an antibody has specific binding affinity for the product of the enzyme but not for the substrate. In another format ("Format 2"), an antibody has specific binding affinity for the substrate of the enzyme but not for the product.

The substrate can be the molecule upon which a suitable ecdysteroid biosynthetic enzyme or homolog directly acts, as well as molecules further upstream in the pathway of ecdysone biosynthesis. See e.g., Gilbert et al., *Control and Biochemical Nature of the Ecdysteroidogenic Pathway,* Ann Rev Entomology (in press). Thus, exemplary substrates include radiolabeled and non-labeled ketotriol (2,22-dideoxyecdysone), ketodiol (2,22,25-trideoxyecdysone), diketol (3-dehydroketodiol), 2dE (2-deoxyecdysone), 22dE (22-deoxyecdysone), E (ecdysone), 20E (20-hydroxyecdysone), C (cholesterol), 25C (25-hydroxycholesterol), 7dC (7-dehydrocholesterol), 7d25C (7-dehydro-25-hydroxycholesterol), sitosterol, fucosterol, and stigmasterol. The product can be the molecule directly produced by a suitable ecdysteroid biosynthetic enzyme or homolog, as well as molecules further downstream in the pathway of ecdysone biosynthesis. Thus, exemplary products include radiolabeled and non-labeled 22dE, 2dE, E, 20E, 26E (26-hydroxyecdysone), 20,26E (20, 26-dihydroxyecdysone), 7dC, 7d25C, "delta"-4-diketol, diketol, ketodiol, ketotriol, fucosterol, fucosterol epoxide stigmasterol epoxide and 5- and/or 11-hydroxyecdysteroids.

Format 1 assays use a product-specific antibody. The antibody is typically immobilized (e.g., on the surface of a 96-well titer plate). Cells or cell extracts containing a suitable ecdysteroid biosynthetic enzyme are incubated in proximity to the antibody along with inhibitor, tracer (i.e., radioactively or enzymatically labeled product), and an appropriate substrate. Control reactions lack inhibitor. Tracer is typically added prior to substrate. Substrate, product and tracer compete for binding to the antibody. The antibody is separated from the unbound components of the reaction and the amount of antibody-bound tracer is measured by scintillation counting for RIA, or by an appropriate enzymatic assay for EIA. If an inhibitor molecule decreases the activity of an ecdysteroid enzyme, there is less displacement of antibody-bound tracer by unlabeled product than in control reactions that lack inhibitor, resulting in higher post-reaction measurements of antibody-bound tracer.

Format 2 assays use a substrate-specific antibody. The antibody is typically immobilized (e.g., on the surface of a 96-well titer plate). Cells or cell extracts containing a suitable ecdysteroid biosynthetic enzyme are incubated with inhibitor and an appropriate substrate. Control reactions lack inhibitor. The reaction mixture is heated to inactivate the enzyme prior to incubation with antibody and tracer (i.e., radioactively or enzymatically labeled substrate). The antibody is separated from the unbound components of the reaction and the amount of antibody-bound tracer is measured by scintillation counting for RIA, or by an appropriate enzymatic assay for EIA. If an inhibitor molecule decreases the activity of an ecdysteroid enzyme, there is more displacement of antibody-bound tracer by unlabeled substrate than in control reactions that lack inhibitor, resulting in lower post-reaction measurements of antibody-bound tracer.

In assays that employ whole cells, the substrate, product and inhibitor are typically freely diffusible within the intact cell preparation. In high throughput assays, all the necessary reagents are incubated together in a 96-well, or larger, format.

In other embodiments of the invention, a suitable ecdysteroid biosynthetic enzyme and a candidate inhibitor molecule are brought into contact with one another in an in vitro biochemical reaction. In these embodiments, enzymes are purified (i.e., extracted from cells and, optionally, separated from various other cellular biomolecules). Means for purifying P450 type enzymes are well known in the art. See e.g., Chen, W. et al, (1996) *Arch Biochem Biophys.,* 335:123–30. Inhibitory effects of purified enzymes can be tested using the same types of assays described above. In some embodiments, a reaction contains only one ecdysteroid biosynthetic enzyme. In other embodiments, a reaction contains one or more additional enzymes in the ecdysteroid biosynthetic pathway.

In another aspect, the invention provides methods for identifying molecules having insecticidal properties. The methods involve contacting an insect with a molecule that inhibits an ecdysteroid biosynthetic enzyme, and determining whether or not the molecule decreases the viability of the insect. If necessary, an ecdysteroid biosynthetic enzyme can be contacted with the candidate molecule to demonstrate inhibition of the enzyme as discussed herein. Insects can be contacted with a candidate inhibitor, for example, by spraying or soaking newly hatched insect larvae with a liquid suspension or powder containing the inhibitor or by feeding newly hatched insect larvae a food adulterated with the candidate inhibitor molecule. A candidate inhibitor decreases the insect viability if larvae contacted with the candidate inhibitor mature to adulthood at a lower frequency than larvae that are not contacted with the candidate inhibitor molecule. For example, if 100 of 1000 larvae contacted with a candidate inhibitor molecule mature to adulthood and 800 of 1000 uncontacted larvae mature to adulthood, the candidate inhibitor decreases insect viability. With respect to an embryo, a non-viable embryo is an embryo that has died.

In another aspect, the invention provides methods for making inhibitors of ecdysteroid synthesis. The method involves contacting a suitable ecdysteroid biosynthetic enzyme with at least one candidate inhibitor molecule, determining whether or not the molecule decreases the activity of the enzyme, and synthesizing a plurality of those molecules that decrease the activity of the enzyme.

In another aspect, the invention provides methods for making an insecticide. The methods involve contacting an insect with the molecule, determining whether or not the molecule decreases the viability of the insect, and synthesizing a plurality of those molecules that decrease the viability of the insect. Chemical inhibitors can be made by a variety of methods known to the skilled artisan. Peptide inhibitors can be made by a variety of methods, including those described in Merrifield (1963) *J. Am. Chem. Soc.,* 85:2149–2154; and U.S. Pat. No. 6,280,595. The latter method can also be used to generate a large library of potential peptide inhibitors.

In another aspect, the invention provides kits for testing whether a molecule affects the activity of an ecdysteroid biosynthetic enzyme. The kits contain one or more of the following: a nucleic acid construct encoding a suitable ecdysone biosynthetic enzyme, a transfected cell containing a suitable ecdysone biosynthetic enzyme, and a suitable ecdysone biosynthetic enzyme. The kits also can contain, separately or in association, one or more of the following: a suitable substrate, a suitable product, a suitable tracer, or a suitable antibody.

Transgenic Organisms

The invention also provides transgenic eukaryotic organisms that express ecdysteroid biosynthetic enzymes substantially identical to the CYP302a1 protein (SEQ ID NO:1), the CYP306a1 protein (SEQ ID NO:2), CYP307a1 protein (SEQ ID NO:3), the CYP314a1 protein (SEQ ID NO:4), and the CYP315a1 protein (SEQ ID NO:5). A transgenic eukaryote of the invention can express any one of the above-mentioned polypeptides or homologs, several of the above-mentioned polypeptides or homologs, or all of the above-mentioned polypeptides or homologs. In some embodiments, a transgenic eukaryote also expresses other enzymes in the ecdysteroid biosynthetic pathway. Such transgenic organisms can serve as a source for enzymes, e.g., for use in the above-described inhibitor screens.

In general, a transgenic organism that expresses an exogenous polypeptide contains a nucleic acid construct that encodes a polypeptide not normally encoded by its genome. The nucleic acid construct is capable of being transcribed in the organism to make mRNA that is then translated to produce the exogenous polypeptide. A transgenic organism can contain one or multiple nucleic acid constructs, and each nucleic acid construct can encode one or multiple exogenous polypeptides.

A nucleic acid construct (e.g., vector) encoding an exogenous polypeptide can be introduced into a eukaryotic organism by a variety of techniques known to those of ordinary skill in this art, such as calcium phosphate or lithium acetate precipitation, electroporation, lipofection, particle bombardment, and electrospraying.

One of skill can screen transgenic organisms to determine whether they have the desired phenotype (e.g., whether the polypeptide encoded by the introduced nucleic acid construct is expressed, and whether an expressed exogenous polypeptide is functional). For example, one can use antibodies to detect expression of the polypeptide. One can also devise assays that measure the activity of the encoded polypeptide. In some applications, the screening method allows large numbers of samples to be processed rapidly, since transgenic organisms often may not have the desired phenotype.

Nucleic Acid Constructs

A nucleic acid encoding a novel polypeptide of the invention may be obtained by, for example, the polymerase chain reaction (PCR). PCR can be used to amplify specific sequences from DNA as well as RNA, including sequences from total genomic DNA or total cellular RNA. Various PCR methods are described, for example, in *PCR Primer: A Laboratory Manual*, eds. Dieffenbach & Dveksler, Cold Spring Harbor Laboratory Press, 1995. Generally, sequence information from the ends of the region of interest or beyond is employed to design oligonucleotide primers that are identical or similar in sequence to opposite strands of the template to be amplified. In addition, various known PCR strategies can be used to introduce site-specific nucleotide sequence modifications into template nucleic acid.

Genes encoding ecdysteroid biosynthetic enzymes can also be chemically synthesized. Manual synthesis of nucleic acid fragments may be accomplished using well-established procedures. For example, a synthetic gene can be enzymatically assembled in a DNA vector from chemically synthesized oligonucleotide duplex segments. Automated chemical synthesis can be performed using various commercially available machines.

To design a synthetic gene for enhanced expression in a target organism, the DNA sequence can be modified from a naturally occurring ecdysteroid biosynthetic polypeptide-encoding gene or designed de novo to: 1) contain codons preferred by highly expressed genes in the target organism; 2) have an A+T content in nucleotide base composition that approximates that of the target organism; 3) have an initiation sequence like those of the target organism; 4) eliminate sequences that cause destabilization, inappropriate polyadenylation, degradation and termination of RNA; and/or 5) avoid sequences that produce secondary structure hairpins and RNA splice sites. Not all of the above-mentioned design features need be incorporated into a synthetic gene in order to obtain enhanced expression. A synthetic gene may be synthesized for other purposes in addition to that of achieving enhanced levels of expression.

In some embodiments, the codons for a synthetic gene reflect the distribution frequency of codon usage of highly expressed genes in the target organism. The distribution frequency of codon usage utilized in the synthetic gene is a determinant of the level of expression. For optimal expression, the synthetic gene is typically designed so that its distribution frequency of codon usage deviates no more than 30% (e.g., 0–10%, 10–20%, 20–30%) from that of highly expressed genes in the target organism. In general, genes within a taxonomic group exhibit similarities in codon choice, regardless of the function of these genes.

In embodiments where a synthetic gene is to be expressed in a dicot plant, a synthetic gene can be designed to incorporate to advantage codons used preferentially by highly expressed dicot proteins. In embodiments where enhanced expression is desired in a monocot, codons preferred by highly expressed monocot proteins are employed in designing the synthetic gene. An estimate of the overall use of the genetic code by a taxonomic group can be obtained by summing codon frequencies of all its sequenced genes. Monocot and dicot codon preferences are analyzed and reported, for example, in U.S. Pat. No. 6,013,523.

In some embodiments, the A+T content in DNA base composition of a synthetic gene reflects that normally found in genes for highly expressed proteins native to the target organsim (e.g., 55–60% in many plants). Typically, the synthetic has an A+T content near this value, and not so high as to cause destabilization of RNA and, thereby, reduce protein expression levels.

For some applications it may be useful to direct exogenous polypeptides to different cellular compartments, or to facilitate its secretion from the cell. To this end, the skilled artisan can make chimeric genes encoding an ecdysteroid biosynthetic enzyme with appropriate intracellular targeting sequences such as transit sequences (Keegstra (1989) *Cell*, 56:247–253), signal sequences or sequences encoding endoplasmic reticulum localization (Chrispeels (1991) *Ann. Rev. Plant Phys. Plant Mol. Biol.*, 42:21–53), or nuclear localization signals (Raikhel (1992) *Plant Phys.*, 100:1627–1632). While the references cited give examples of each of these, the list is not exhaustive and additional targeting signals of use may be discovered in the future.

Nucleic acid constructs may contain cloning vector segments. Cloning vector segments are commercially available and are used routinely by those of ordinary skill. Nucleic acid constructs of the invention may also contain sequences encoding other polypeptides. Such polypeptides may, for example, facilitate the introduction or maintenance of the nucleic acid construct into a host organism. Such polypeptides may also be used to facilitate the introduction of the nucleic acid construct into a target organism. Other polypeptides may also affect the expression, activity, or biochemical or physiological effect of the encoded CBF polypeptide. Alternatively, other polypeptide coding sequences may be provided on separate nucleic acid constructs.

Nucleic acid constructs may also contain one or more regulatory elements operably linked to an ecdysteroid biosynthetic enzyme coding sequence. Such regulatory elements may include promoter sequences, enhancer sequences, response elements, protein recognition sites, or inducible elements that modulate expression of a nucleic acid sequence. As used herein, "operably linked" refers to positioning of a regulatory element in a construct relative to a nucleic acid coding sequence in such a way as to permit or facilitate expression of the encoded polypeptide. The choice of element(s) that may be included depends upon several factors, including, but not limited to, replication efficiency, selectability, inducibility, desired expression level, and cell or tissue specificity.

Suitable regulatory elements include promoters that initiate transcription only in certain cell types. In some embodiments, a cell type or tissue-specific promoter may also drive transcription of operably linked sequences in additional cell types or tissues. Other useful promoters may drive transcription in the same cell type or tissue through more than one developmental stage.

In some embodiments, a nucleic acid construct contains a promoter and a recognition site for a transcriptional activator, both of which are operably linked to the coding sequence for an ecdysteroid biosynthetic enzyme. In these embodiments, transgenic organisms that express the ecdysteroid biosynthetic enzyme contain a second nucleic acid construct that encodes a transcriptional activator. A transcriptional activator is a polypeptide that binds to a recognition site on DNA, resulting in an increase in the level of transcription from a promoter associated in cis with the recognition site.

The recognition site for the transcriptional activator polypeptide is positioned with respect to the promoter so that upon binding of the transcriptional activator to the recognition site, the level of transcription from the promoter is increased. The position of the recognition site relative to the promoter can be varied for different transcriptional activators, in order to achieve the desired increase in the level of transcription.

Many transcriptional activators have discrete DNA binding and transcription activation domains. The DNA binding domain(s) and transcription activation domain(s) of transcriptional activators can be synthetic or can be derived from different sources (e.g., two-component system or chimeric transcriptional activators). In some embodiments, a two-component system transcriptional activator has a DNA binding domain derived from the yeast gal4 gene and a transcription activation domain derived from the VP16 gene of herpes simplex virus. Populations of transgenic organisms or cells having a first nucleic acid construct that encodes a chimeric polypeptide and a second nucleic acid construct that encodes a transcriptional activator polypeptide can be produced by transformation, transfection, or genetic crossing. See, e.g., WO 97/31064.

For some applications, it may be desirable to reduce or eliminate expression of genes encoding the instant polypeptides in a target organism for some applications. To this end, a skilled artisan can employ antisense RNA or cosuppression technologies. An "antisense" molecule generally contains nucleic acids or nucleic acid analogs that can specifically hybridize to a target nucleic acid. It is understood in the art that the sequence of an antisense molecule need not be 100% complementary to that of its target nucleic acid to be specifically hybridizable. An antisense oligonucleotide is specifically hybridizable when (a) binding of the molecule to the target DNA or RNA interferes with the normal function of the target DNA or RNA, and (b) there is sufficient complementarity to avoid non-specific binding of the antisense molecule to non-target sequences under conditions in which specific binding is desired, i.e., under conditions in which in vitro assays are performed or under physiological conditions for in vivo assays or therapeutic uses.

The specific hybridization of an antisense molecule with its target nucleic acid can interfere with the normal function of the target nucleic acid. For a target DNA, an antisense molecule can disrupt replication and transcription. For a target RNA, an antisense molecule can disrupt, for example, translocation of the RNA to the site of protein translation, translation of protein from the RNA, splicing of the RNA, and catalytic activity of the RNA. The overall effect of such interference with target nucleic acid function is, in the case of a nucleic acid encoding an ecdysteroid biosynthetic enzyme, modulation of the expression of a ecdysteroid biosynthetic enzyme. In the context of the present invention, "modulation" means a decrease in the expression of a gene and/or a decrease in cellular levels of the protein encoded by a gene.

Plants

Among the eukaryotic organisms provided by the invention are transgenic plants that express ecdysteroid biosynthetic enzymes substantially identical to the CYP302a1 protein (SEQ ID NO:1), the CYP306a1 protein (SEQ ID NO:2), CYP307a1 protein (SEQ ID NO:3), the CYP314a1 protein (SEQ ID NO:4), and the CYP315a1 protein (SEQ ID NO:5).

Techniques for introducing exogenous nucleic acids into monocotyledonous and dicotyledonous plants are known in the art, and include, without limitation, *Agrobacterium*-mediated transformation, viral vector-mediated transformation, electroporation and particle gun transformation, e.g., U.S. Pat. Nos. 5,204,253 and 6,013,863. If a cell or tissue culture is used as the recipient tissue for transformation, plants can be regenerated from transformed cultures by techniques known to those skilled in the art. Transgenic plants may be entered into a breeding program, e.g., to introduce a nucleic acid encoding a polypeptide into other lines, to transfer the nucleic acid to other species or for further selection of other desirable traits. Alternatively, transgenic plants may be propagated vegetatively for those species amenable to such techniques. Progeny includes descendants of a particular plant or plant line. Progeny of an instant plant include seeds formed on $F_1$, $F_2$, $F_3$, and subsequent generation plants, or seeds formed on $BC_1$, $BC_2$, $BC_3$, and subsequent generation plants. Seeds produced by a transgenic plant can be grown and then selfed (or outcrossed and selfed) to obtain seeds homozygous for the nucleic acid encoding a novel polypeptide.

A suitable group of plants with which to practice the invention include dicots, such as safflower, alfalfa, soybean, rapeseed (high erucic acid and canola), or sunflower. Also suitable are monocots such as corn, wheat, rye, barley, oat, rice, millet, amaranth or sorghum. Also suitable are vegetable crops or root crops such as potato, broccoli, peas, sweet corn, popcorn, tomato, beans (including kidney beans, lima beans, dry beans, green beans) and the like. Thus, the invention has use over a broad range of plants, including species from the genera *Anacardium, Arachis, Asparagus, Atropa, Avena, Brassica, Citrus, Citrullus, Capsicum, Carthamus, Cocos, Coffea, Cucumis, Cucurbita, Daucus, Elaeis, Fragaria, Glycine, Gossypium, Helianthus, Heterocallis, Hordeum, Hyoscyamus, Lactuca, Linum, Lolium, Lupinus, Lycopersicon, Malus, Manihot, Majorana, Medicago, Nicotiana, Olea, Oryza, Panicum, Pannesetum, Persea, Phaseolus, Pistachia, Pisum, Pyrus, Prunus, Raphanus, Ricinus, Secale, Senecio, Sinapis, Solanum, Sorghum, Theobromus, Trigonella, Triticum, Vicia, Vitis, Vigna* and *Zea*.

Ecdysteroid biosynthetic enzymes can be expressed in plants in a cell- or tissue-specific manner according to the regulatory elements chosen to include in a particular nucleic acid construct introduced into the plant. Suitable cells, tissues and organs in which to express an ecdysteroid biosynthetic enzyme include, without limitation, embryo, cotyledons, endosperm, seed coat, vascular bundle, cambium, phloem, cortex, floral tissue, root tissue, leaf mesophyll cells, and leaf epidermal cells.

In some embodiments, a promoter that is specific to a plant vegetative tissue such as vascular bundle, cambium, phloem, cortex, leaf mesophyll, or leaf epidermis directs transcription of an ecdysone biosynthetic enzyme. In other embodiments, a promoter that is specific to a plant reproductive tissue such as fruit, ovule, seed, flower, endosperm directs transcription of an ecdysone biosynthetic enzyme. Methods for identifying and characterizing promoter regions in plant genomic DNA include, for example, those described in the following references: Jordano et al., (1989) *Plant Cell*, 1:855–866; Bustos et al., (1989) *Plant Cell*, 1:839–854; Green et al., (1988) *EMBO J.*, 7:4035–4044; Meier et al., (1991) *Plant Cell*, 3, 309–316; and Zhang et al., (1996) *Plant Physiology*, 110:1069–1079.

Exemplary plant reproductive tissue promoters include those derived from the following genes: *Brassica napus* 2 s storage protein (see, Dasgupta (1993) *Gene*, 133:301–302); *Arabidopsis* 2 storage protein; soybean β-conglycinin; *Brassica napus* oleosin 20kD gene (see, GenBank No. M63985); soybean oleosin A (see, Genbank No. U09118); soybean oleosin B (see, GenBank No. U09119); *Arabidopsis* oleosin (see, GenBank No. Z17657); maize oleosin 18 kD (see, GenBank No. J05212; Lee (1994) *Plant Mol. Biol.*, 26:1981–1987; the gene encoding low molecular weight sulfur rich protein from soybean, (see, Choi (1995) *Mol. Gen, Genet.*, 246:266–268); and fruit-specific E8, a tomato gene expressed during fruit ripening, senescence and abscission of leaves and flowers (Blume (1997) *Plant J.*, 12:731-746). See also, WO 98/08961; WO 98/28431; WO 98/36090; U.S. Pat. No. 5,907,082; and WO 00/24914.

Exemplary plant vegetative tissue promoters include those derived from the following genes: potato storage protein patatin gene (see, Kim (1994) *Plant Mol. Biol.*, 26:603–615; Martin (1997) *Plant J.*, 11:53–62); root Agrobacterium rhizogenes ORF13 (see, Hansen (1997) *Mol. Gen. Genet.*, 254:337–343); genes active during taro corm development (see, Bezerra (1995) *Plant Mol. Biol.*, 28:137–144); de Castro (1992) *Plant Cell*, 4:1549–1559); root meristem and immature central cylinder tobacco gene TobRB7 (see, Yamamoto (1991) *Plant Cell*, 3:371–382); ribulose biphosphate carboxylase genes RBCS1, RBCS2, and RBCS3A expressed in tomato leaves (see, Meier (1997) *FEBS Lett.*, 415:91–95); ribulose biphosphate carboxylase genes expressed in leaf blade and leaf sheath mesophyll cells (see, Matsuoka (1994) *Plant J.*, 6:311–319); leaf chlorophyll a/b binding protein (see, e.g., Shiina (1997) *Plant Physiol.*, 115:477–483; Casal (1998) *Plant Physiol.*, 116:1533–1538); *Arabidopsis* Atmyb5, expressed in developing leaf trichomes, stipules, in epidermal cells on the margins of young rosette and cauline leaves, and in immature seeds between fertilization and the 16 cell stage of embryo development and persists beyond the heart stage (see, Li (1996) *FEBS Lett.*, 379:117–121); and a maize leaf-specific gene described by Busk (1997) *Plant J.*, 11:1285–1295.

Cell type or tissue-specific promoters derived from viruses can also be suitable regulatory elements. Exemplary viral promoters include: the tobamovirus subgenomic promoter (Kumagai (1995) *Proc. Natl. Acad. Sci. USA*, 92:1679–1683; the phloem-specific tungro bacilliform virus (RTBV) promoter; the cassaya vein mosaic virus (CVMV) promoter, expressed most strongly in vascular elements, leaf mesophyll cells, and root tips (Verdaguer (1996) *Plant. Mol. Biol.*, 31:1129–1139).

The invention will be further described in the following examples, which do not limit the scope of the invention described in the claims.

EXAMPLES

Example 1

Mutations in dib, spo, shd, sad and phm Affect *Drosophila* Morphogenesis

Wild type and mutant *Drosophila* strains, available from the Bloomington *Drosophila* Stock Center (Indiana University), were cultured on standard cornmeal/yeast extract/dextrose medium. At particular stages of development, embryos were stained with spectrin antibody. Mutations in dib, spo, shd, sad, and phm were observed to prevent full differentiation of the embryonic cuticle. dib, spo, shd, sad, and phm embryos appeared to develop normally to approximately stage 14. At this point, many morphogenetic movements including dorsal closure, head involution, midgut morphogenesis and hindgut looping become abnormal. In particular, no denticle belts, dorsal hairs or differentiated mouth parts were evident in dib, spo, shd, sad, and phm homozygotes. Only a thin cuticular remnant containing both dorsal and anterior holes was secreted by most of the mutant embryos.

Embryos were also stained with Acridine orange, DAPI and reaper to examine whether there was an increase in apoptosis during these late stages. Neither unusual DAPI staining, nor increased numbers of AO-positive or reaper-expressing cells were observed, suggesting that abnormal numbers of cells were not dying during this time.

To determine if the abnormal morphogenesis phenotypes were caused by removal of maternal components, germline clones were made. Homozygous mutant germline clones were generated in the background of a dominant female-sterile mutant ovo D. For example, virgin females w, hs-Flp/ w: FRT79, dib F8/TM3 were crossed to males FRT79, ovo D w+/TM3. The first instar larvae of this exemplary cross were heat shocked at 37° C. for 90 minutes and the non TM3 females were crossed to males dib P3/TM3, ftz-lacZ. Eggs were stained with anti-β-gal antibody in order to distinguish the homozygous dib germline clone embryos from the heterozygous embryos.

Embryos derived from mutant germlines exhibited exactly the same range and timing of defects as did simple zygotic mutants, suggesting that dib, spo, shd, sad, and phm are not required in the germline during oogenesis or during early embryogenesis before stage 14.

Example 2

Identification of a Novel P450 Gene

The dib locus is localized to the 64A3 interval on the left arm of the third *Drosophila* chromosome. A phage walk spanning about 30 kb was established in the region. Several cDNAs were isolated and positioned within the walk by Southern hybridization analysis and sequencing. P-element-mediated transformation was used to make transgenic lines carrying various overlapping genomic DNA fragments. P elements carrying DNA from several phages were able to rescue the l(3)64Ak complementation group, previously shown to be allelic to dib. A single transcription unit defined by a 1.7 kb cDNA was localized to the DNA contained on each of these phages.

The 1.7 kb cDNA was sequenced, and conceptual translation of the Dib product revealed that it is a new member of the cytochrome P450 superfamily. Genomic DNA obtained from lines carrying three different dib alleles was also sequenced. Each dib allele resulted from the introduction of a stop codon. See FIG. 1.

Example 3 dib, spo, shd, sad and phm Display Reduced ECD-dependent Transcription

Expression of the 20E-inducible genes IMP-E1 and L1 in wild type and in dib, spo, shd, sad and phm mutant embryos was observed by whole-mount RNA in situ hybridization and antibody staining. IMP-E1 and L1 encode novel secreted proteins that respond either directly (IMP-E1) (i.e., inducible in the presence of cycloheximide), or indirectly (IMP-L1), to 20E in culture. Both genes are expressed in complex patterns in the embryo. Since the timing of the epidermal expression coincides with the rise in embryonic ecdysteroid titers, these patterns were examined in wild type and in dib, spo, shd, sad and phm mutant backgrounds.

Embryos were fixed for 20 minutes in a 1:2 mixture of PBS:heptane that contained 4% formaldehyde. Devitellinizing was accomplished by washing the embryos several times in methanol. Imaginal disks and ovaries were dissected into phosphate-buffered saline (PBS), fixed in 4% formaldehyde and stored in ethanol at about 20° C. until use. Sense and anti sense digoxigenin-labeled RNA probes (Boehringer Mannheim) were generated by transcription of pBluescript dib, IMP-E1 or L1 subclones using T3, T7 or the Sp6 promoter. Embryos collected from heterozygotes containing a balancer chromosome marker with either Ubx-lacZ (for third chromosome mutants), or wg-lacZ (for second chromosome mutants), were double stained with anti-β-gal antibody and RNA probe in order to distinguish the homozygous mutants from those that carried the lacZ balancer chromosome. RNA hybridization and detection was carried out using standard methods. The rabbit anti-Spectrin antibody (a gift from T. Hays) was used at 1/100 dilution and the mouse β-gal monoclonal antibody (Promega) was used at 1/1000 dilution. Staining for both antibodies was visualized using an HRP-coupled secondary antibody (Vector Laboratories) and diaminobenzidine as substrate. Embryos, disks and ovaries were mounted for photography in 10% PBS and 90% glycerol.

Epidermal expression of both IMP-E1 and IMP-L1 was observed to be greatly reduced or absent in dib, spo, shd, sad and phm mutant backgrounds.

Example 4 dib, spo, shd, sad and phm Mutants Display Reduced ECD and 20E Titers

Levels of ECD and 20E in 7- to 16-hour old embryos were measured by an enzyme immunoassay (i.e., EIA). Embryos were collected from parents heterozygous for each of the mutant strains (in this example, dib F8) and from a TM3 balancer marked with a arm-GFP reporter. Embryos were sorted by fluorescence into GFP-negative pools containing the dib homozygous mutant embryos and a GFP-positive pool corresponding to dib/TM2, arm-GFP heterozygotes and TM2, arm-GFP homozygotes. Embryos were dechorionated and frozen at about 20° C. until used.

Embryos were homogenized in 0.5 ml of methanol and incubated at 4° C. for 2 hours. The supernatant was saved and the embryos were again incubated in 0.5 ml methanol overnight. Both supernatants were pooled and dried under $N_2$. Ecdysteroids were analyzed with an enzyme immunoassay modified from that of Porcheron et al. (1989) *Insect Biochem.*, 19:117–122, using a 20-hydroxyecdysone-peroxidase conjugate as a tracer and either DBL2-polyclonal anti-ECD antiserum or EC19 monoclonal anti-20E antibodies (see Aribi et al. (1997) *Biochim. Biophys. Acta*, 1335: 246–252; Pascual et al. (1995) *Z. Naturforsch.*, [C] 50:862–7). Briefly, dried samples were solubilized in a phosphate buffer (0.1 M, pH 7.4), placed on microplate wells (previously coated with secondary anti-IgG antibodies), then a known amount of tracer was added along with the primary anti-ecdysteroid antibody. After a 3-hour incubation at room temperature, bound peroxidase activity was revealed using tetramethylbenzidine as substrate and microplates were analyzed using a SpectraMax 340 microplate reader (Molecular Devices). Results were compared with data obtained from reference concentrations of ecdysone or 20-hydroxyecdysone and were normalized to the weight of the samples.

Homozygous mutants contained very low concentrations of both E and 20E, compared to control embryos. The results for the dib and spo mutants are shown below in Tables 1 and 2. The residual low levels of these products seen in the homozygous mutants could correspond to either remaining maternal products, to other metabolites weakly recognized by the antibodies, or to low-level synthesis of each product by another less-efficient pathway.

TABLE 1

Ecdysteroid levels measured by EIA on single pools of 7- to 12-hour homo- or heterozygous dib embryos

| Phenotypes | dib/dib | dib/gfp | Oregon (WT) |
|---|---|---|---|
| Pool size (mg) | 26 | 71.1 | 8.1–112 |
| ECD-equivalents (pg/mg), using L2 polyclonal serum | 1.52 (±0.18; n = 8) | 11.04 (±0.59; n = 8) | 15.35 (±1.19; n = 6) |
| 20E-equivalents (pg/mg), using EC19 mAb | 0.71 (±0.11; n = 3) | 2.92 (±0.05; n = 3) | 3.68 (±0.25; n = 3) |

Results expressed as pg equivalents. For dib/dib and dib/GFP embryos the same sample was measured several times (3–8 replicates) and the results are expressed as a mean ± the standard deviation. Statistical analysis by Student's t-test indicates that the two experimental pool means differ from that of the control population ($P < 0.05$).

TABLE 2

Ecdysteroid levels measured by EIA on single pools of 7- to 16-hour homo- or heterozygous spo embryos

| Phenotypes | spo/spo | spo/gfp | Oregon (WT) |
|---|---|---|---|
| Pool size (mg) | 18.8 | 57 | 45 |
| ECD-equivalents (pg/mg), using L2 polyclonal serum | 5.3 (±0.5) | 17.8 (±0.5) | 26.1 (±0.2) |
| 20E-equivalents (pg/mg), using EC19 mAb | 0 (*) | 11.9 (±0.2) | 28.2 (±2.6) |

(*) Values were below the detection limit of the method. For each sample, 6 replicates have been measured, allowing calculation of the standard error of the corresponding pool mean (indicated by ±).

Example 5

Activity of CYP302a1, CYP306a1, CYP307a1, CYP314a1, & CYP315a1

Schneider line-2 cells (S2 cells) were grown in M3 medium (Shields and Sang M3 insect medium, Sigma) with 10% insect medium supplement (IMS, Sigma) and 1% penicillin/streptomycin (Gibco BRL). A DNA-DDAB (dimethyldioctadecyl-ammonium bromide) mixture was prepared as described by Han (1996) *Nucleic Acid Res.*, 24:4362–4363. DDAB suspension (250 µg/ml) was mixed with M3 in a 1:2 ratio and left at room temperature for 5 min. A series of microfuge tubes was prepared, each containing 670 ng of cDNA (dib, spo, shd, sad, and phm; GFP cDNA was used as a control) in pUAST plasmid. DDAB/M3 mixture (140 µl per tube) was added to each microfuge tube and incubated at room temperature for 15 min. S2 cell suspension was prepared at $2.7 \times 10^6$ cells/ml and split into a titer plate. Immediately after plating, DDAB/M3/DNA mixtures were transferred to the wells. The S2 cells were incubated at 25° C. for 72 hours.

At 72 hours, the medium was aspirated and replaced with 1 ml/well of M3 medium with an appropriate substrate. Cells transfected with dib, sad, phm, and shd were incubated with tritiated 2,22-dideoxyecdysone, 2,22,25-trideoxyecdysone, 25-hydroxycholeserol, or ECD (200,000–300,000 cpm/well). Cells transfected with shd and spo were incubated with 10 µg of unlabelled cholesterol, desmosterol, sitosterol, or fucosterol. The incubation was stopped at 2 hours and 8 hours. The S2 cells were scraped from the wells and transferred to 2 ml cryogenic vials. Two additional washes were done with 400 µl PBS and 400 µl methanol, and the contents transferred to the vials, which were then frozen at −80° C.

Methanol extracts were analyzed by HPLC, and reaction products were identified based on their mobility characteristics relative to standards. CYP302a1, encoded by dib, can catalyze the conversion of 2,22-dideoxyecdysone to 2-deoxyecdysone. See FIG. 2. CYP315a1, encoded by sad, can convert 2,22-dideoxyecdysone to 22-deoxyecdysone. See FIG. 3. CYP315a1 can also convert 2-deoxyecdysone to ecdysone. The spo, shd and phm genes appear to encode enzymes that catalyze earlier steps in the ecdysteroid biosynthetic pathway.

Example 6

Screen for Inhibitors of CYP302a1

A Format 2 assay is used to identify inhibitors of CYP302a1. A substrate-specific antibody is immobilized in the wells of a 96-well titer plate, along with a tracer. The antibody binds 2,22-dideoxyecdysone and has a very low cross-reactivity for 2-deoxyecdysone. The tracer is synthesized from 2,22-dideoxyecdysone. For an EIA, the labeling enzyme (e.g., peroxidase) is linked to 2,22-dideoxyecdysone via the C3 or C6 functionalities. *Drosophila* S2 cells transfected with the dib gene are incubated with 2,22-dideoxyecdysone and various inhibitors in a separate 96-well titer plate. After the reaction is complete, the reaction mixture is heated to inactivate the CYP302a1 enzyme and the reactions are discretely transferred to the wells of antibody-coated titer plate. Following this incubation, the wells are aspirated and washed. In RIA, scintillant is added to the wells and antibody-bound radiolabeled tracer is measured. In EIA, following the washing step, substrate for the labeling enzyme is added to the antibody-bound tracer and following incubation, the product is quantified (e.g., by UV absorption for peroxidase conjugate tracers).

Example 7

Screen for Inhibitors of CYP315a1

A Format 1 assay is used to identify inhibitors of CYP315a1. A product-specific antibody, Horn H22, is immobilized in the wells of a 96-well titer plate. It is able to bind ecdysone and has a very low cross-reactivity for 2-deoxyecdysone. *Drosophila* S2 cells transfected with the sad gene are added to the antibody-coated wells. Various inhibitors are added to the wells for pre-incubation with the S2 cells, along with ecdysone tracer. For an EIA, a labeling enzyme (e.g., peroxidase) is linked via the side-chain at carbon 22 or carbon 26. Unlabeled 2-deoxyecdysone is then added to the wells. The wells are aspirated and washed. In RIA, scintillant is added to the wells and antibody-bound 3H-ECD is measured. In EIA, following the washing step, a substrate for the labeling enzyme is simply added to the antibody-bound tracer and following incubation, the product is quantified (e.g., by UV absorption for peroxidase conjugate tracers).

OTHER EMBODIMENTS

It is to be understood that while the invention has been described in conjunction with the detailed description thereof, the foregoing description is intended to illustrate and not limit the scope of the invention.

TABLE 3

Novel P450 Enzyme Amino Acid and cDNA sequences

CYP302a1 protein (SEQ ID NO: 1)

MLTKLLKISCTSRQCTFAKPYQAIPGPRGPFGMGNLYNYLPGIGSYSWLRLHQAGQDKYEKYGAIVRETIVPGQDIVWLYDPK

DIALLLNERDCPQRRSHLALAQYRKSRPDVYKTTGLLPTNGPEWWRIRAQVQKELSAPKSVRNFVRQVDGVTKEFIRFLQESR

NGGAIDMLPKLTRLNLELTSLLTFGARLQSFTAQEQDPSSRSTRLMDAAETTNSCILPTDQGLQLWRFLETPSFRKLSQAQSY

MEGVAMELVEENVRNCSVGSSLISAYVKNPELDRSDVVGTAADLLLAGIDTTSYASAFLLYHIARNPEVQQKLHEEAKRVLPS

AKDELSMDALRTDITYTRAVLKESLRLNPIAVGVGRILNQDAIFSGYFVPKGTTVVTQNMVRCRLEQHFQDPLRFQPDRWLQH

RSALNPYLVLPFGHGMRACIARRLAEQNMHILLLRLLREYELIWSGSDDEMGVKTLLINKPDAPVLIDLRLRRE

CYP302a1 cDNA (SEQ ID NO:6)

CGTTGCTGTCGGAATTTGCCGCGAAAAGACCAGAGTAACGACGAAAAATGTTGACCAAACTGTTAAAGATTAGCTGCACCTCG

AGGCACTGCACCTTTGCCAAGCCGTATCAGGCGATACCAGGACCACGAGGACCCTTTGGAATGGGTAATCTATACAATTACCT

GCCCGGAATCGGATCCTATTCCTGGCTAAGATTGCACCAAGCCGGCCAGGATAAGTATGAGAAATATGGCGCAATTGTGCGGG

AAACTATAGTTCCTGGGCAGGACATTGTCTGGTTGTACGATCCCAAGGACATAGCTTTGCTGCTCAACCAGCCGGATTGTCCG

CAGCGAAGAAGTCACCTGCCACTGGCTCAATATCGCAAGAGCCGACCGGATGTCTATAAAACCACCGGCTTGCTGCCCACCAA

TGGTCCGGAATGGTGGCGTATACGTGCCCAGGTGCAAAAGGAGCTGAGTGCACCAAAGAGTGTGCGGAACTTCGTTCGCCAAG

TGGATGGAGTGACCAAGGAGTTCATTAGATTTCTACAAGAATCTCGCAATGGTGGTGCCATTGATATGCTGCCCAAGCTCACC

AGATTGAATTTGGAATTAACCTCTTTGCTTACCTTTGGAGCCCGTCTGCAGTCTTTTACTGCCCAGGAACAAGATCCTAGTTC

CCGATCCACTCGCTTGATGGATGCGGCCGAGACCACCAATAGCTGCATCCTGCCCACAGATCAGGGCCTCCAGCTGTGGCGAT

TTCTGGAGACACCTAGCTTTCGCAAACTAAGCCAGGCCCAATCATATATGGAGGGTGTGGCCATGGAGTTAGTGGAGGAGAAT

GTTAGGAATGGTTCAGTGGGATCTTCACTGATCTCGGCTTATGTAAAAAATCCCGAGCTTGATCGCACTGACGTGGTGGGCAC

CGCTGCAGATTTACTCTTGGCTGGCATCGATACCACTTCGTATGCCTCGGCATTTCTGCTCTATCACATAGCTCGAAATCCGG

AGGTGCAGCAAAAACTGCACGAGGAGGCCAAGAGAGTGCTTCCGAGTGCCAAGGACGAGCTATCCATGGATGCCCTACGAACT

GATATCACCTATACGAGGGCTGTCCTCAAGGAATCACTACGCTTGAATCCCATTGCCGTGGGCGTGGGCAGGATTCTTAATCA

GGATGCGATCTTCAGTGGCTACTTCGTGCCAAAGGGGACCACCGTGGTTACCCAGAACATGGTACGCTGCCGGCTGGAGCAGC

ACTTCCAGGATCCCCTGCGCTTCCAACCAGATCGATGGCTCCAGCACCGTAGTGCCCTCAATCCCTATCTGGTCCTTCCCTTC

GGTCACGGAATGCGGGCCTGCATTGCCCGCCGTTTGGCCGAGCAGAATATGCACATTTTGCTTCTCAGGCTGCTGCGTGAATA

CGAATTGATTTGGAGCGGATCCGATGATGAGATGGGTGTGAAGACCCTGTTGATAAATAAACCCGATGCTCCAGTGCTGATCG

ATCTGCGATTGCGTAGAGAATAAGGTTATTAGGTATAAGTAAGTCGCCAGAGCCTTAAGACTGAGATACTAGACTCGTGTCAC

GTTTAAATAATTCGTTTATTAATTATTTTAAATTAGCTCATAATTAATTATAATTAGTGTAAATTATATATAACTAGACTTGC

ATTTTATGTGATTGAAAGGCTGTGGGTGTTTTGGTCTAAGTACTAAAGAGAACGACTAAAAGGCAAAAAAAAAAAAAAA

CYP306a1 protein (SEQ ID NO:2)

MSADIVDIGHTGWMPSVQSLSILLVPGALVLVILYLCERQCNDLMGAPPPGPWGLPFLGYLPFLDARAPHKSLQKLAKRYGGI

TABLE 3-continued

Novel P450 Enzyme Amino Acid and cDNA sequences

FELKMGRVPTVVLSDAALVRDFFRRDVMTGRAPLYLTHGIMGGFGIICAQEDIWRHARRETIDWLKALGMTRRPGELRARLER
RIARGVDECVRLFDTEAKKSCASEVNPLPALHHSLGNIINDLVFGITYKRDDPDWLYLQRLQEEGVKLIGVSGVVNFLPWLRH
LPANVRNIRFLLEGKAKTHAIYDRIVEACGQRLKEKQKVFKELQEQKRLQRQLEKEQLRQSKEADPSQEQSEADEDDEESDEE
DTYEPECILEHFLAVRDTDSQLYCDDQLRHLLADLFGAGVDTSLATLRWFLLYLAREQRCQRRLHELLLPLGPSPTLEELEPL
AYLRACISETMRIRSVVPLGIPHGCKENFVVGDYFIKGGSMIVCSEWAIHMDPVAFPEPEEFRPERFLTADGAYQAPPQFIPF
SSGYRMCPGEEMARMILTLFTGRILRRFHLELPSGTEVDMAGESGITLTPTPHMLRFTKLPAVEMRHAPDGAVVQD

CYP306a1 cDNA (SEQ ID NO:7)
ATGTCGGCGGACATCGTCGATATTGGCCACACCGGTTGGATGCCCTCGGTGCAGAGCCTGAGTATTCTGCTGGTTCCGGGTGC
GCTCGTCCTGGTGATTCTCTACCTGTGCGAGCGCCAGTGCAATGACCTCATGGGTGCCCCACCGCCGGGTCCCTGGGGCCTGC
CCTTTCTGGGTTACCTGCCCTTCCTGGACGCCCGTGCGCCGCACAAGTCACTCCAGAAGCTGGCCAAGCGGTATGGTGGAATT
TTCGAGCTGAAAATGGGCAGGGTGCCGACCGTAGTCCTCTCGGATGCCGCCTTGGTGCGGGATTTCTTTCGGCGCGATGTGAT
GACTGGCCGTGCGCCGCTCTACCTCACCCACGGCATCATGGGTGGATTTGGCATCATCTGCGCCCAGGAGGACATTTGGCGAC
ATGCACGGCGCGAGACTATCGATTGGCTAAAGGCCTTGGGCATGACCCGTCGGCCGGGGGAACTGCGCGCGCGGCTCGAGCGG
CGCATAGCCCGCGGAGTCGACGAGTGCGTACGGCTTTTCGATACTGAGGCAAAGAAGAGCTGTGCGTCGGAAGTGAATCCGCT
GCCGGCGCTCCATCACTCGCTGGGCAACATAATCAACGACCTGGTCTTCGGGATCACCTACAAGCGCGACGACCCCGACTGGC
TGTACCTGCAGCGGCTGCAGGAGGAGGGCGTCAAGCTGATTGGCGTCTCCGGGGTGGTCAACTTTTTGCCCTGGCTGCGTCAC
CTGCCCGCCAACGTGCGCAACATCCGCTTCCTGCTGGAGGGCAAGGCCAAGACGCACGCCATCTACGACCGCATTGTGGAGGC
CTGTGGCCAGCGGCTGAAGGAGAAGCAGAAGGTGTTCAAGGAGCTCCAGGAGCAGAAGCGGCTGCAAAGGCAGCTAGAGAAGG
AGCAGCTCAGGCAGTCAAAGGAAGCGGATCCAAGCCAGGAGCAGAGTGAGGCAGACGAGGATGACGAGGAGAGCGATGAGGAG
GACACGTACGAGCCGGAGTGCATCCTGGAGCACTTCCTAGCCGTTCGAGACACGGATTCGCAGCTCTACTGCGACGACCAGCT
GCGCCATCTGCTGGCCGATCTCTTTGGAGCCGGGGTGGACACCTCGCTGGCCACCCTGCGCTGGTTCCTGCTCTACTTGGCCC
GCGAACAACGCTGCCAGCGGCGCCTGCATGAGCTCCTCCTGCCGCTGGGTCCGTCTCCCACTTTGGAGGAACTGGAGCCGCTG
GCCTACCTAAGGGCTTGCATTTCCGAGACGATGCGCATACGCAGCGTTGTCCCACTGGGCATTCCGCACGGATGCAAAGAGAA
CTTCGTCGTGGGCGATTATTTTATCAAGGGTGGTTCGATGATCGTTTGCTCGGAGTGGGCTATCCACATGGACCCAGTGGCCT
TCCCGGAACCGGAGGAGTTCCGTCCGGAGCGCTTCTTGACCGCCGATGGAGCCTACCAGGCGCCGCCACAGTTCATCCCATTC
TCGTCCGGCTATCGAATGTGTCCCGGCGAAGAGATGGCTCGCATGATACTCACGCTCTTTACGGGTCGCATCCTCAGGCGCTT
CCACTTGGAACTGCCCTCGGGCACTGAGGTGGACATGGCGGGTGAGAGCGGCATCACCCTGACCCCCACTCCGCACATGCTGC
GATTCACCAAGCTGCCGGCGGTGGAGATGCGCCATGCACCCGACGGAGCTGTGGTGCAGGATTAG

CYP307a1 protein (SEQ ID NO:3)
MLAALIYTILAILLSVLATSYICIIYGVKRRVLQPVKTKNSTEINHNAYQKYTQAPGPRPWPIIGNLHLLDRYRDSPFAGFTA
LAQQYGDIYSLTFGHTRCLVVNNLELIREVLNQNGKVMSGRPDFIRYHKLFGGERSNSLALCDWSQLQQKRRNLARRHCSPRE
SSCFYMKMSQIGCEEMEHWNRELGNQLVPGEPINIKHLILKACANMFSQYMCSLRFDYDDVDFQQIVQYFDEIFWEINQGHPL
DFLPWLYPFYQRHLNKIINWSSTIRGFIMERIIRHRELSVDLDEPDRDFTDALLKSLLEDKDVSRNTIIFMLEDFIGGHSAVG
NLVMLVLAYIAKNVDIGRRIQEEIDAITEEKNRSINLLDMNAMPYTMATIFEVLRYSSSPIVPHVATEDTVISGYGVTKGTIV
FINNYVLNTSEKFWVNPKEFNPLRFLEPSKEQSPKNSKGSDSGIESDNEKLQLKRNIPHFLPFSIGKRTCIGQNLVRGFGFLV
VVNVMQRYNISSHNPSTIKISPESLALPADCFPLVLTPREKIGPL CYP307a1 cDNA (SEQ ID NO:8)
AGTTGTGTTTTGTGCTTCCTACTTTCAAGAGCTCAGCAAAAATGCTGGCTGCTTTGATTTACACTATTTTGGCGATTTTACTG
AGTGTTCTGGCCACGTCCTACATATGCATTATATATGGAGTCAAGCGCCGCGTTCTGCAGCCCGTTAAAACAAAGAATTCAAC TABLE 3-continued Novel P450 Enzyme Amino Acid and cDNA sequences

```
CGAAATCAATCACAATGCTTATCAAAAATATACCCAGGCTCCAGGACCACGACCATGGCCCATCATTGGTAATCTTCATCTGC
TGGATCGATACAGGGATAGTCCCTTTGCGGGATTCACGGCGTTGGCACAGCAATACGGAGACATATACTCCCTGACCTTCGGA
CACACCCGCTGTCTGGTGGTGAACAACTTGGAGCTGATCCGCGAGGTGCTCAATCAAAATGGCAAGGTGATGAGCGGGCGGCC
AGACTTCATACGATATCATAAACTATTTGGTGGCGAGCGAAGCAATTCGTTGGCTCTGTGCGATTGGTCACAGCTGCAGCAGA
AGAGAAGGAATCTGGCCAGGCGTCACTGCTCGCCCAGGGAATCTTCCTGCTTCTACATGAAAATGTCCCAGATTGGTTGCGAG
GAAATGGAGCACTGGAATCGGGAGCTGGGAAACCAACTCGTTCCTCGAGAGCCGATCAACATCAAGCATCTGATTCTGAAGGC
CTGTGCAAATATGTTTAGTCAGTACATGTGTTCGTTGAGGTTCGACTACGATGATGTGGACTTCCAACAGATTGTTCAATACT
TCGATGAGATATTCTGGGAAATCAATCAGGGACATCCGCTGGATTTTCTACCCTGGCTATATCCCTTCTACCAGCGACACCTG
AACAAGATCATCAACTGGTCCTCGACTATCAGGGGATTCATAATGGAAAGGATTATCCGGCATCGGGAGCTGAGCGTCGATTT
GGATGAACCAGATCGGGACTTCACAGATGCTCTACTTAAAAGCCTGCTTGAAGATAAAGATGTCTCCCCGGCAACGATTATCT
TCATGCTCGAGGATTTCATTGGTGGACATTCAGCGGTTGGAAATCTAGTAATGCTAGTGCTGGCCTATATAGCCAAAAATGTG
GATATTGGAACGAGAATACAAGAGGAAATTGACCCAATTACTGAAGAGAAAATAGGTCAATTAATTTGCTGGACATGAATGC
TATGCCCTACACGATCGCGACGATTTTCGAGGTGCTGCCATATTCATCCTCCCCAATTCTTCCACATGTGGCCACCGAGCACA
CAGTGATCTCTGGCTATGGGGTACCAAGGGCACCATTGTGTTCATCACAATTATGTGCTAAACACCAGCGAGAGAAATTCTCG
GTAAATCCCAAGGAATTTAATCCATTAAGATTTTTGGAACCGTCAAAGGAACAAAGCCCAAAAAATTCCAAAGGTTCTGATTC
TGGCATCGAAAGTGATAATGAAAAACTTCAACTAAAGAGCAATATTCCGCACTTTCTGCCCTTTAGCATCGCGAAGCGGACTT
GCATCGGCCACAATTTGGTGAGAGGATTTGGTTTTCTGGTCGTGGTCAACGTAATGCAGAGATATAATATCAGCAGTCATAAT
CCTTCGACGATTAAGATCAGTCCGGAGAGTTTGGCACTCCCTGCCGATTGTTTTCCATTGGTCTTGACACCCAGGGAAAAGAT
CGGACCACTATAATAAATTATAAATTAAAAACCAATACCATTAAGCACTAGCAATTAAAATATTACACATAAATAGCCCAAAC
AGCTTCAGAATAAGATTACTGCGTTATCTATTATCAGACATAACGAATAAGCTCAATCAAATAGTAAAACTATTTTACTGTTG
AGTATATTTTCAATTACTTAACGCAAATACAAAATTTTTGTATTTCATGTCTATATTTTGTACGATACCAAACACGCAAAGTC
TTATAGATGCTCACCACACTATAAAAATTTCACATACATTCGATTCTTGAGGATCTTAGGATTAGATTAATTCGTTAAGAACT
TCGTTACAGTAAATGACTCAAATATGTATAATGTGCACGCCGATGTAAAATTCAAGTGTAATTCTTAAGCGAAATATTTACAA
TTTTTATTTTCTTTTAGAATCAATAAATGTGGGCCCACATGGGCCTTATATAAATGACATAGAAACCTAAAGCTGAATAAAAT
CCAAAA
```

CYP314a1 protein (SEQ ID NO:4)

MAVILLLALALVLGCYCALHRHKLDIYLLRPLLKNTLLEDFYHAELIQPEAPKRRRRGIWDIPGPKRIPFLGTKWIFLLFFRR

YKMTKLHEVYADLNRQYGDIVLEVMPSNVPIVHLYNRDDLEKVLKYPSKYPFRPPTEIIVMYRQSRPDRYASVGIVNEQGPMW

QRLRSSLTSSITSPRVLQNPLPALNAVCDDFIELLRARRDPDTLVVPNFEELANLMGLEAVCTLMLGRRMGFLAIDTKQPQKI

SQLAAAVKQLFISQRDSYYGLGLWKYFPTKTYRDFARAEDLIYDVISEIIDHELEELKKSAACEDDEAAGLRSIFLNILELKD

LDIRDKKSAIIDFIAAGIETLANTLLFVLSSVTGDPGAMPRILSEFCEYRDTNILQDALTNATYTKACIQESYRLRPTAFCLA

RILEEDMELSGYSLNAGTVVLCQNNIACHKDSNFQCAKQFTPERWIDPATENFTVNVDNASIVVPFGVGRRSCPGKRFVEMEV

VLLLAKMVLAFDVSFVKPLETEFEFLLAPKTPLSLRLSDRVF

CYP314a1 cDNA (SEQ ID NO:9)

```
ATGGCCGTGATACTGTTGCTGGCCCTCGCACTCGTACTTGTCTGCTACTGCGCTCTCCATCCGCACAAATTGGCGGATATCTA
CCTCCGGCCGCTCCTGAAGAACACGCTCCTTGAGGACTTCTACCATGCCGAGCTGATCCAGCCCGAGGCGCCAAAGAGGCGCA
GGCGCCGCATCTCGGACATACCCGGGCCAAAGAGGATTCCCTTCCTGCCCACTAAGTGGATATTCCTCCTCTTCTTCGACCG
TACAAGATGACCAAGCTGCACCAGGTATATGCGGATTTGAACAGACAATATGGGCACATAGTGCTGGAGCTGATCCCCTCCAA
TGTGCCAATAGTGCACCTGTACAATCGCGATGATCTGGAGAAGGTGCTGAAGTACCCCAGCAAATACCCATTCCGACCTCCCA
```

TABLE 3-continued

Novel P450 Enzyme Amino Acid and cDNA sequences

```
CCGAGATCATCGTGATGTACCGTCAGTCCCGACCGGATCGCTATGCAAGTGTTGGAATTGTGAATGAGCAAGGACCAATGTGG
CAGCGCCTACCATCTTCCCTGACCTCCAGCATTACTTCTCCCCGGGTCCTGCAGAATTTCCTGCCAGCCTTGAATGCGGTTTG
TCATCATTTTACCGAACTACTCCGAGCCAGGCGGGATCCGCATACACTGGTGGTTCCCAATTTCGAAGAGCTGGCCAATCTGA
TGGGTCTGGAAGCTGTGTGCACTTTAATGCTGGGCAGAAGGATGGGTTTCCTGGCTATCGATACCAAGCAGCCGCAAAACATA
AGCCAACTGGCAGCTGCTGTTAAACAGCTTTTCATATCCCAAAGGGACTCGTACTACGGTCTGGGTCTGTGGAAATACTTTCC
CACCAAAACCTACAGAGACTTTGCCCGCGCCGAGGACTTGATCTATGATGTGATCTCCGAGATCATCGATCATGAGCTGGAGG
AACTCAAAACGTCCGCTGCCTGCGAGGATGACGAGGCTGCTGGATTACGAAGTATCTTTCTGAATATTCTCGAGCTCAAGGAT
CTGGATATCAGCGACAAAAACTCAGCGATCATAGACTTTATTGCCGCTGGCATAGAAACGTTAGCCAACACTTTCTTCTTTGT
ACTGAGTTCTGTTACTGCACATCCCGGTGCTATGCCACCAATCCTAAGTGAATTCTGCGAGTATCGGGACACGAATATCCTGC
AGGATGCACTAACGAATGCCACATACACAAAGGCCTGTATACAGGAGTCCTACAGACTGAGGCCCACAGCCTTTTGCCTGCCC
AGAATCCTGGAGGAGGACATGGAGCTCTCGGGCTACTCGCTTAATGCACGGACTGTGGTGCTCTGTCAGAATATGATAGCCTG
CCACAAGGACAGCAACTTCCAAGGGGCCAAGCAGTTTACCCCAGAGCGTTGGATTGATCCTGCCACGCAGAATTTCACGGTGA
ACGTCGGATAATGCCACTATTGTGGTGCCCTTCGCAGTGGGTCGAGCCATCGTGTCCAGGAGCGTTTTGTGGAAATGGAGGTG
GTGCTGCTGCTAGCTAAGATGGTCCTAGCCTTTCATGTGAGCTTTGTGAAGCCACTGGAAACGGAGTTCGACTTCCTGCTGGC
ACCCAAAACTCCACTCAGTCTAAGACTCAGCCATCGGGTTTTCTGA
```

CYP315a1 protein (SEQ ID NO:5)

```
MTEKRERPGPLRWLRHLLDQLLVRILSLSLFRSRCDPPPLQRFPATELPPAVAAKYPIPRVKGLPVVGTLVDLIAACGGATHL
HKYIDARHKQYGPIFRERLGGTQDAVFVSSANLMRGVFQHEGQYPQHPLPDAWTLYNQQHACQRGLFFMEGAEWLHNRRILNR
LLLNGNLNWMDVHIESCTRRMVDQWKRRTAEAAAIPLAESGEIRSYELPLLEQQLYRWSIEVLCCIMFGTSVLTCPKIQSSLD
YFTQIVHKVFEHSSRLMTFPPRLAQILRLPIWRDFEANVDEVLREGAAIIDHCIRVQEDQRRPHDEALYHRLQAADVPGDMIK
RIFVDLVTAAGDTTAFSSQWALFALSKEPRLQQRLAKERATNDSRLMHGLIKESLRLYPVAPFIGRYLPQDAQLGGHFIEKDT
MVLLSLYTAGRDPSHFEQPERVLPERWCIGETEQVHKSHGSLPFAIGQRSCIGRRVALKQLHSLLGRCAAQFEMSCLNEMPVD
SVLRMVTVPDRTLRLALRPRTE
```

CYP315a1 cDNA (SEQ ID NO:10)

```
GCGCGGAGTCTTCCAGCACGAGGGTCAGTATCCGCAGCATCCGCTGCCGGATGCCTGGACGCTGTATAACCAGCAACATGCCT
GCCAACGGGGACTGTTCTTCATGGAGGGCGCCGAGTGGCTGCACAACCGACGCATACTTAATCGACTGCTGCTCAACGGAAAT
TTGAATTGGATGGACGTGCATATTGAGAGCTGTACCACACGAATGGTGGATCAGTGGAAAAGACGCACTGCGGAGGCGGCGGC
GATTCCGCTAGCGGAGAGTGGTGAAATACGAAGCTACGAACTGCCCCTGTTGGAACAACAGCTCTACCGTTGGTCCATAGAAG
TTCTGTGCTGCATCATGTTTGGCACCAGCGTGCTCACCTGCCCCAAGATCCAGTCCTCGCTGGACTACTTCACGCAGATTGTG
CACAAGGTGTTTGAGCATAGCTCGCGACTGATGACATTCCCGCCTCGCTTGGCCCAGATTTTGCGCCTGCCCATCTGGCGGGA
TTTCGAGGCCAATGTGGATGAGGTGCTGCGTGAGGGAGCTGCCATAATCGATCACTGCATCAGAGTGCAGGAGGACCAAAGGA
GACCGCACGATGAGGCGCTTTACCATCGCCTCCAGGCGGCGGATGTGCCAGGCGATATGATCAAGCGGATATTTGTAGACTTG
GTCATTGCAGCAGGTGACACGACCGCATTCAGCAGTCAGTGGGCTTTGTTTGCCCTTTCAAAGGAGCCGAGGCTCCAGCAACG
ACTGGCCAAGGAGCGAGCTACCAATGATTCTCGCCTGATGCACGGCCTGATCAAGGAGTCCCTGCGTCTGTACCCCGTAGCTC
CCTTCATTGGCCGATATCTGCCGCAGGACGCGCAACTTGGCGGTCACTTTATCGAAAAGGATACCATGGTGCTGCTCTCCTTG
TACACGGCAGGTCGCGATCCATCACACTTTGAGCAGCCGGAACGTGTGCTCCCGGAGCGCTGGTGCATTGGAGAGACGGAGCA
GGTGCATAAGTCACACGGCAGTCTGCCTTTTGCCATCGGCCAGCGGTCTTGCATTGGTCGCCGTGTGGCACTCAAGCAGCTCC
ACTCCCTGCTGGGCCGATGTGCTGCTCAGTTTGAGATGAGCTGCCTTAACGAGATGCCCGTTGACAGCGTACTCCGCATGGTC
```

TABLE 3-continued

Novel P450 Enzyme Amino Acid and cDNA sequences

ACCGTGCCCGATCGGACTTTGCGTTTAGCCCTTCGGCCGCGAACCGAGTGA

---

What is claimed is:

1. A method for identifying inhibitors of ecdysteroid synthesis, said method comprising:
   contacting a purified ecdysteroid biosynthetic enzyme with a candidate inhibitor molecule; and
   determining whether or not said molecule inhibits the activity of said enzyme,
   wherein said enzyme has an amino acid sequence substantially identical to the amino acid sequence of SEQ ID NO:4, wherein said enzyme exhibits ecdysteroid biosynthetic activity in the absence of said candidate inhibitor molecule.

2. The method of claim 1, wherein said determining step uses a product-specific antibody or a substrate-specific antibody.

3. The method of claim 2, wherein said product-specific antibody or said substrate-specific antibody is attached to a solid substrate.

4. The method of claim 3, wherein said solid substrate is a microtiter plate.

* * * * *